United States Patent
Asahara et al.

(10) Patent No.: US 9,316,660 B2
(45) Date of Patent: Apr. 19, 2016

(54) REAGENT PREPARATION APPARATUS AND SPECIMEN PROCESSING SYSTEM

(75) Inventors: Tomoyuki Asahara, Kobe (JP); Kouichi Ookubo, Kobe (JP); Noriyuki Nakanishi, Kakogawa (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 13/218,956

(22) Filed: Aug. 26, 2011

(65) Prior Publication Data

US 2011/0311396 A1 Dec. 22, 2011

Related U.S. Application Data

(63) Continuation of application No. PCT/JP2010/053065, filed on Feb. 26, 2010.

(30) Foreign Application Priority Data

Feb. 27, 2009 (JP) .................................. 2009-46588

(51) Int. Cl.
  *G01N 1/28* (2006.01)
  *B01L 99/00* (2010.01)
  (Continued)

(52) U.S. Cl.
  CPC ............ *G01N 35/10* (2013.01); *G01N 35/0092* (2013.01); *G01N 35/00663* (2013.01); *G01N 35/00732* (2013.01); *G01N 2035/00465* (2013.01); *G01N 2035/00673* (2013.01)

(58) Field of Classification Search
  CPC .............. G01N 35/0092; G01N 35/10; G01N 35/0063; G01N 35/00732; G01N 2035/00673; G01N 2035/00465

USPC .............. 422/62, 67, 68.1, 82.01; 435/287.3; 436/43
  See application file for complete search history.

(56) References Cited

U.S. PATENT DOCUMENTS

| 5,800,056 A | 9/1998 | Suzuki et al. |
| 7,381,370 B2 | 6/2008 | Chow et al. |
| 7,670,554 B2 | 3/2010 | Chow et al. |

(Continued)

FOREIGN PATENT DOCUMENTS

| CN | 1826218 A | 8/2006 |
| JP | 06-207944 A | 7/1994 |

(Continued)

OTHER PUBLICATIONS

International Search Report for International Application No. PCT/JP2010/053065, dated May 18, 2010, 2 pages.

(Continued)

Primary Examiner — Jill Warden
Assistant Examiner — Julie Tavares
(74) Attorney, Agent, or Firm — Brinks Gilson & Lione

(57) ABSTRACT

This reagent preparation apparatus prepares a reagent supplied to a measurement portion measuring a specimen with the reagent. The reagent is prepared from a first liquid and a second liquid different from the first liquid. The reagent preparation apparatus comprises a reagent preparation portion preparing the reagent and a control portion acquiring reagent information related to the reagent prepared by the reagent preparation portion, acquiring supply time information related to a time when the reagent prepared by the reagent preparation portion was supplied to the measurement portion and outputting the reagent information and the supply time information.

14 Claims, 18 Drawing Sheets

(51) Int. Cl.
*G01N 35/10* (2006.01)
*G01N 35/00* (2006.01)

(56) References Cited

U.S. PATENT DOCUMENTS

| | | |
|---|---|---|
| 8,257,650 B2 | 9/2012 | Chow et al. |
| 2001/0044761 A1 | 11/2001 | Berger et al. |
| 2005/0207936 A1* | 9/2005 | Berryhill et al. ............ 422/63 |
| 2007/0118422 A1 | 5/2007 | Berger et al. |
| 2007/0212261 A1* | 9/2007 | Tanaka et al. ............ 422/67 |

FOREIGN PATENT DOCUMENTS

| | | |
|---|---|---|
| JP | 09-033538 A | 2/1997 |
| JP | 2002-032642 A | 1/2002 |
| JP | 2002-277451 A | 9/2002 |
| JP | 2007-240430 A | 9/2007 |
| WO | WO 94/11838 A1 | 5/1994 |

OTHER PUBLICATIONS

Extended European Search Report for European Application No. 10746316.8, dated Nov. 4, 2013, 9 pages.

* cited by examiner

HIGH-CONCENTRATION REAGENT INFORMATION
ACQUISITION PROCESSING

FIG.12 REAGENT PREPARATION PROCESSING

FIG.18

| | | REFERENCE | ELECTRODE | THERMISTOR |
|---|---|---|---|---|
| DATE | TIME | VALUE | VALUE | VALUE |
| '09/01/05 | 10:03 | 9999 | 9999 | 9999 |
| '09/01/05 | 10:10 | 9999 | 9999 | 9999 |
| .... | ... | ... | ... | ... |
| '09/02/05 | 10:15 | 9999 | 9999 | 9999 |
| .... | ... | ... | ... | ... |

STANDBY | REAGENT SUPPLIABLE | Help
[PREPARATION HISTORY]

483a, 484, 483c, 483d, 483b, 483e (HISTORY CLEAR), 483f (RETURN)

FIG.19

STANDBY | REAGENT SUPPLIABLE | Help
[PREPARATION HISTORY]

| DATE | TIME | LOT No. | POST-PREPARATION EXPIRATION DATE | USE START DAY | POST-OPENING EXPIRATION DATE |
|---|---|---|---|---|---|
| '09/01/05 | 10:03 | A8020 | '09/04/30 | '09/01/05 | '09/02/04 |
| '09/01/05 | 10:10 | A8020 | '09/04/30 | '09/01/05 | '09/02/04 |
| .... | ... | ... | .... | .... | .... |
| '09/02/05 | 10:15 | A8021 | '09/05/30 | '09/02/05 | '09/03/07 |
| .... | ... | ... | .... | .... | .... |

483a, 485, 483c, 483d, 483b, 483e (HISTORY CLEAR), 483f (RETURN)

REAGENT PREPARATION APPARATUS AND SPECIMEN PROCESSING SYSTEM

RELATED APPLICATIONS

This application is a continuation of PCT/JP2010/053065 filed on Feb. 26, 2010, which claims priority to Japanese Application No. 2009-046588 filed on Feb. 27, 2009. The entire contents of these applications are incorporated herein by reference.

BACKGROUND OF THE INVENTION

1. Field of the Invention

The present invention relates to a reagent preparation apparatus and a specimen processing system, and more particularly, it relates to a reagent preparation apparatus and a specimen processing system each capable of preparing a reagent employed for measurement.

2. Description of the Related Art

In general, a reagent preparation apparatus capable of preparing a reagent employed for measurement is known (refer to Japanese Patent Laying-Open No. 9-33538, for example).

A reagent preparation apparatus capable of preparing a reagent consisting of a high-concentration reagent and pure water is disclosed in Japanese Patent Laying-Open No. 9-33538.

If the reliability of a measurement result is low in a case of performing measurement with the reagent prepared by the reagent preparation apparatus, it is required to pursue the cause thereof and to make an improvement. As one of the items to be confirmed for pursuing the cause of the reduction in the reliability of the measurement result, reagent information related to the reagent employed for the measurement is conceivable.

However, Japanese Patent Laying-Open No. 9-33538 gives no description about a structure acquiring reagent information related to the reagent prepared by the reagent preparation apparatus. In this reagent preparation apparatus, therefore, it is conceivable that the reagent information of the reagent employed for the measurement cannot be obtained in the case where the reliability of the measurement result is low, and hence there is such a problem that it is difficult to perform pursuance of the cause of the reduction in the reliability of the measurement result.

Therefore, a technique capable of acquiring reagent information related to a reagent prepared by reagent preparation apparatus is known in general (refer to Japanese Patent Laying-Open No. 2007-240430, for example).

A centralized surveillance system including a plurality of reagent preparation apparatuses, a server computer connected to the plurality of reagent preparation apparatuses and a client computer connected to the server computer is disclosed in Japanese Patent Laying-Open No. 2007-240430. This centralized surveillance system is so formed that reagent information such as electric conductivity of a reagent prepared by the reagent preparation apparatus and preparation date information of the reagent are transmitted from each reagent preparation apparatus to the server computer and the transmitted reagent information and preparation date information are displayable on the client computer.

SUMMARY OF THE INVENTION

In the centralized surveillance system described in Japanese Patent Laying-Open No. 2007-240430, however, it is impossible to confirm when the prepared reagent has been employed in a measurement portion while it is possible to confirm the reagent information and the preparation date information of the reagent prepared by the reagent preparation apparatus, and hence it is difficult to specify the reagent employed for the measurement in the case where the reliability of the measurement result is low. Also in this centralized surveillance system, therefore, there is such a problem that pursuance of the cause of the reduction in the reliability of the measurement result cannot be easily performed.

The present invention has been proposed in order to solve the aforementioned problem, and an object of the present invention is to provide a reagent preparation apparatus and a specimen processing system each capable of easily performing pursuance of a cause of reduction in the reliability of a measurement result.

In order to attain the aforementioned object, a reagent preparation apparatus according to a first aspect of the present invention is a reagent preparation apparatus comprising: a reagent preparation portion preparing a reagent from a first liquid and a second liquid different from the first liquid, wherein the reagent is supplied to a measurement portion measuring a specimen with the reagent; and a control portion acquiring reagent information related to the reagent prepared by the reagent preparation portion, acquiring supply time information related to a time when the reagent prepared by the reagent preparation portion was supplied to the measurement portion and outputting the reagent information and the supply time information.

In the reagent preparation apparatus according to the first aspect of the present invention, as hereinabove described, the control portion acquiring the reagent information related to the reagent prepared by the reagent preparation portion, acquiring the supply time information related to the time when the reagent prepared by the reagent preparation portion was supplied to the measurement portion and outputting the reagent information and the supply time information is so provided that when and what sort of reagent was supplied to the measurement portion can be easily confirmed on the basis of the reagent information of the reagent and the supply time information of the reagent to the measurement portion output by the control portion. Thus, it becomes easy to acquire information of a reagent employed for measurement in a case where the reliability of a measurement result is low, whereby pursuance of the cause of the reduction in the reliability of the measurement result becomes easy.

Preferably in the aforementioned reagent preparation apparatus according to the first aspect, the control portion acquires quality information indicating the quality of the reagent as the reagent information. According to this structure, the quality of the reagent can be confirmed after specifying the prescribe reagent employed for the measurement in the measurement portion, whereby the pursuance of the cause of the reduction in the reliability of the measurement result can be more easily performed.

Preferably in this case, the reagent preparation apparatus further includes an electric conductivity measurement portion measuring electric conductivity of the reagent, and the control portion acquires the electric conductivity measured by the electric conductivity measurement portion as the quality information. According to this structure, the quality of the reagent can be easily determined on the basis of the electric conductivity of the reagent employed for the measurement in the measurement portion.

Preferably in the aforementioned reagent preparation apparatus according to the first aspect, the control portion further acquires preparation time information related to a time when the reagent was prepared by the reagent preparation portion, and acquires the supply time information on the basis of the acquired preparation time information. According to this structure, the supply time information can be acquired by the control portion on the basis of the preparation time information, whereby the supply time information need not be measured and acquired separately from the preparation time information.

Preferably in this case, the reagent preparation apparatus further includes a reagent storage portion storing the reagent prepared by the reagent preparation portion and being in a standby state for supply to the measurement portion, and the control portion acquires a time when the reagent is supplied to the reagent storage portion as the preparation time information. According to this structure, a preparation completion time when the reagent entered a state suppliable to the measurement portion can be regarded as the preparation time information.

Preferably in the aforementioned structure including the reagent storage portion, the reagent preparation apparatus further includes an electric conductivity measurement portion measuring electric conductivity of the reagent transported to the reagent storage portion, and the control portion decides the time when the reagent is supplied to the reagent storage portion on the basis of a time when the reagent transported to the reagent storage portion passes through the electric conductivity measurement portion. According to this structure, the time when the reagent, which is transported to the reagent storage portion after preparation, passes through the electric conductivity measurement portion can be regarded as the preparation time information as the time when the reagent is supplied to the reagent storage portion.

Preferably in the aforementioned structure including the reagent storage portion, the control portion acquires the preparation time information every time the reagent is supplied to the reagent storage portion, and acquires the supply time information on the basis of a plurality of acquired preparation time data. According to this structure, the supply time information can be acquired on the basis of the plurality of preparation time data including preparation time information of the current reagent supplied to the reagent storage portion and preparation time information of a non-current reagent supplied to the reagent storage portion, whereby the supply time information can be more precisely acquired.

Preferably in the aforementioned reagent preparation apparatus according to the first aspect, the control portion acquires a time zone having a possibility that the reagent was supplied to the measurement portion as the supply time information. According to this structure, the reagent having a possibility of being actually employed for the measurement in the measurement portion can be more easily specified, whereby the pursuance of the cause of the reduction in the reliability of the measurement result becomes easier.

Preferably in this case, the reagent preparation apparatus further includes a reagent storage portion storing the reagent prepared by the reagent preparation portion and being in a standby state for supply to the measurement portion, wherein the reagent storage portion has a storage volume, and the time zone having the possibility that the reagent to be specified was supplied to the measurement portion is a time zone from a time when the reagent to be specified began to be supplied to the reagent storage portion up to a time when the reagent in a volume substantially identical to the storage volume of the reagent storage portion was discharged from the reagent storage portion to the measurement portion. According to this structure, the starting time and the ending time of the time zone having the possibility that the reagent was supplied to the measurement portion can be rendered clear, whereby the time zone having the possibility that the reagent was supplied to the measurement portion can be easily acquired by the control portion.

Preferably in the aforementioned reagent preparation apparatus according to the first aspect, the first liquid is an undiluted reagent, and the control portion acquires undiluted reagent information related to the undiluted reagent as the reagent information, and outputs the undiluted reagent information. According to this structure, it is possible to easily confirm which undiluted reagent was used for preparing the reagent employed for the measurement on the basis of the undiluted reagent information of the undiluted reagent contained in the reagent, whereby the pursuance of the cause of the reduction in the reliability of the measurement result becomes easier.

Preferably in this case, the reagent preparation apparatus further includes an information read portion reading the undiluted reagent information from a reagent vessel storing the undiluted reagent, and the control portion acquires the undiluted reagent information on the basis of a result read by the information read portion. According to this structure, the undiluted reagent information can be easily acquired by employing the information read portion.

Preferably in the aforementioned structure in which the first liquid is the undiluted reagent, the undiluted reagent information includes a lot number of the undiluted reagent. According to this structure, it is possible to easily specify which lot of undiluted reagent was used for preparing the reagent employed for the measurement according to the lot number.

Preferably in the aforementioned structure in which the first liquid is the undiluted reagent, the undiluted reagent information includes expiration date information related to the expiration date of the undiluted reagent. According to this structure, whether or not the reagent employed for the measurement is a reagent prepared with an undiluted reagent passing the expiration date can be confirmed.

A reagent preparation apparatus according to a second aspect of the present invention is a reagent preparation apparatus, comprising: a reagent preparation portion preparing a reagent from a first liquid and a second liquid different from the first liquid, wherein the reagent is supplied to a measurement portion measuring a specimen with the reagent, reagent information acquisition means for acquiring reagent information related to the reagent prepared by the reagent preparation portion, supply time information acquisition means for acquiring supply time information related to a time when the reagent prepared by the reagent preparation portion was supplied to the measurement portion and output means for outputting the reagent information and the supply time information.

In the reagent preparation apparatus according to the second aspect of the present invention, as hereinabove described, the reagent information acquisition means acquiring the reagent information related to the reagent prepared by the reagent preparation portion, the supply time information acquisition means acquiring the supply time information related to the time when the reagent prepared by the reagent preparation portion was supplied to the measurement portion and the output means outputting the reagent information and the supply time information are so provided that when and what sort of reagent was supplied to the measurement portion can be easily confirmed on the basis of the reagent information of the reagent and the supply time information of the reagent to the measurement portion output by the control portion. Thus, it becomes easy to acquire information of a reagent employed for measurement in a case where the reliability of a measurement result is low, whereby pursuance of the cause of the reduction in the reliability of the measurement result becomes easy.

A reagent preparation apparatus according to a third aspect of the present invention includes: a reagent preparation portion preparing a reagent from a substance and a liquid, wherein the reagent is supplied to a measurement portion measuring a specimen with the reagent; and a control portion acquiring reagent information related to the reagent prepared by the reagent preparation portion, acquiring supply time information related to a time when the reagent prepared by the reagent preparation portion was supplied to the measurement portion, and outputting the reagent information and the supply time information.

A specimen processing system according to a fourth aspect of the present invention includes a reagent preparation portion preparing a reagent from a first liquid and a second liquid different from the first liquid, a measurement portion measuring a specimen with the reagent prepared by the reagent preparation portion and a control portion acquiring reagent information related to the reagent prepared by the reagent preparation portion, acquiring supply time information related to a time when the reagent prepared by the reagent preparation portion was supplied to the measurement portion and outputting the reagent information and the supply time information.

In the specimen processing system according to the fourth aspect of the present invention, as hereinabove described, the control portion acquiring the reagent information related to the reagent prepared by the reagent preparation portion, acquiring the supply time information related to the time when the reagent prepared by the reagent preparation portion has been supplied to the measurement portion and outputting the reagent information and the supply time information is so provided that when and what sort of reagent was supplied to the measurement portion can be easily confirmed on the basis of the reagent information of the reagent and the supply time information of the reagent to the measurement portion output by the control portion. Thus, it becomes easy to acquire information of a reagent employed for measurement in a case where the reliability of a measurement result is low, whereby pursuance of the cause of the reduction in the reliability of the measurement result becomes easy.

BRIEF DESCRIPTION OF THE DRAWINGS

FIG. 18 is a diagram for illustrating the method of confirming the reagent preparation history in the reagent preparation apparatus according to the first embodiment of the present invention.

FIG. 19 is a diagram for illustrating the method of confirming the reagent preparation history in the reagent preparation apparatus according to the first embodiment of the present invention.

DETAILED DESCRIPTION OF THE PREFERRED EMBODIMENTS

Figure 1:
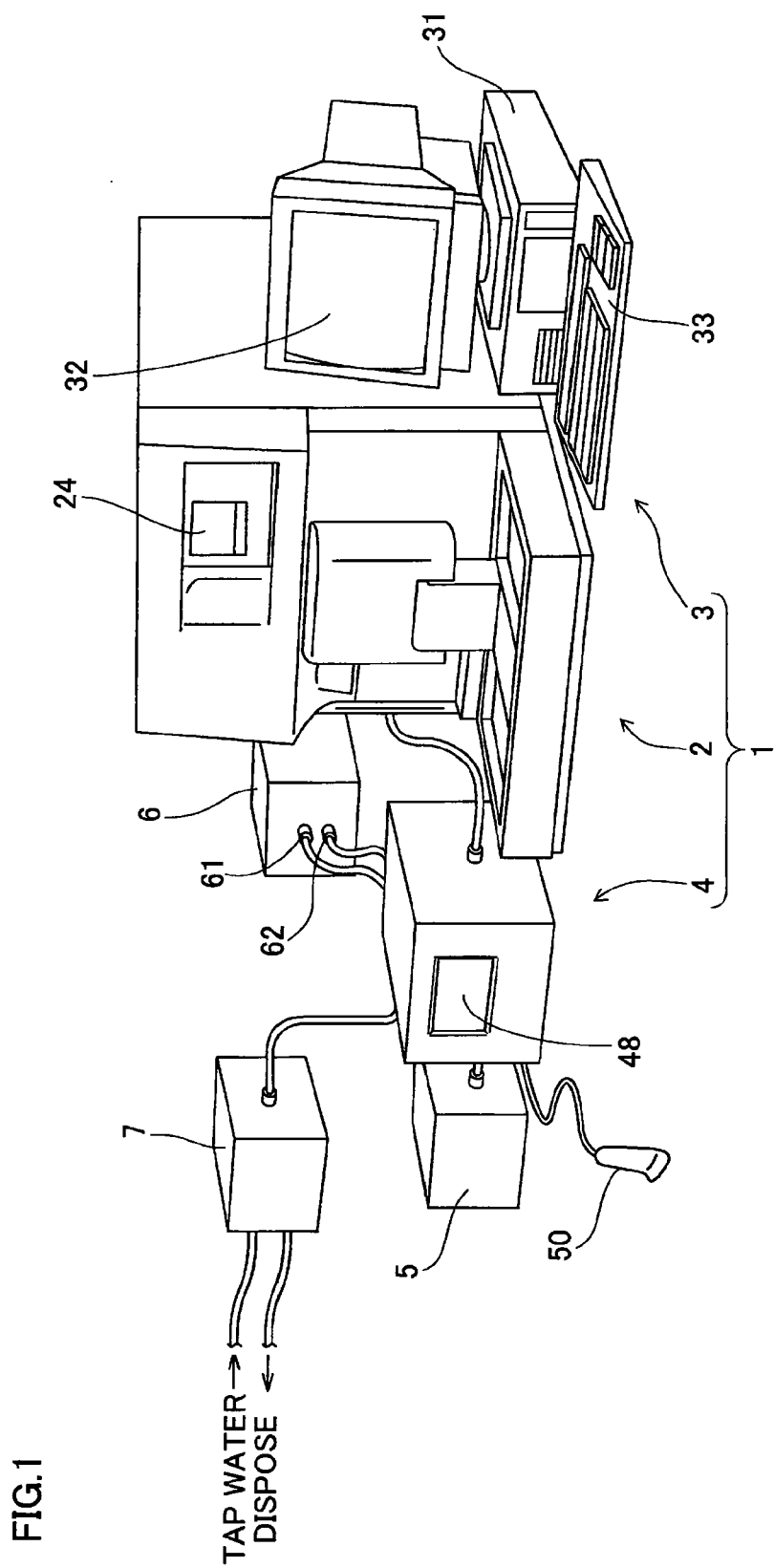
FIG. 1 is a perspective view showing a used state of a reagent preparation apparatus according to a first embodiment of the present invention.

Embodiments of the present invention are now described with reference to the drawings.

First Embodiment

First, the structure of reagent preparation apparatus 4 according to a first embodiment of the present invention is described with reference to FIGS. 1 to 8. In the first embodiment, a case of using the reagent preparation apparatus 4 according to the first embodiment of the present invention as part of a blood specimen processing system 1 for conducting a blood test is described.

The blood specimen processing system 1 is constituted of a measurement portion 2 having a function of performing measurement of blood, a data processing portion 3 analyzing measurement data output from the measurement portion 2 and obtaining an analytical result and the reagent preparation apparatus 4 preparing a reagent employed for processing a specimen. The measurement portion 2 is formed to perform measurement of leukocytes, reticulocytes and platelets in the blood by flow cytometry. Further, the measurement portion 2 is formed to dilute the blood with the reagent prepared and supplied by the reagent preparation apparatus 4 and to perform the measurement of the leukocytes, the reticulocytes and the platelets. In addition, the measurement portion 2 is formed to employ the aforementioned reagent prepared and supplied by the reagent preparation apparatus 4 as a detergent for washing a sampling valve 21b and a reaction chamber 21c included in a sample preparation portion 21 described later, a sheath flow cell 22c included in a detection portion 22 and the like. The flow cytometry is a method of measuring particles (blood cells) by forming a sample stream containing a measurement sample and applying a laser beam to the sample stream thereby detecting forward scattered light, lateral scattered light and lateral fluorescence emitted by the particles (blood cells) in the measurement sample.

Figure 2:
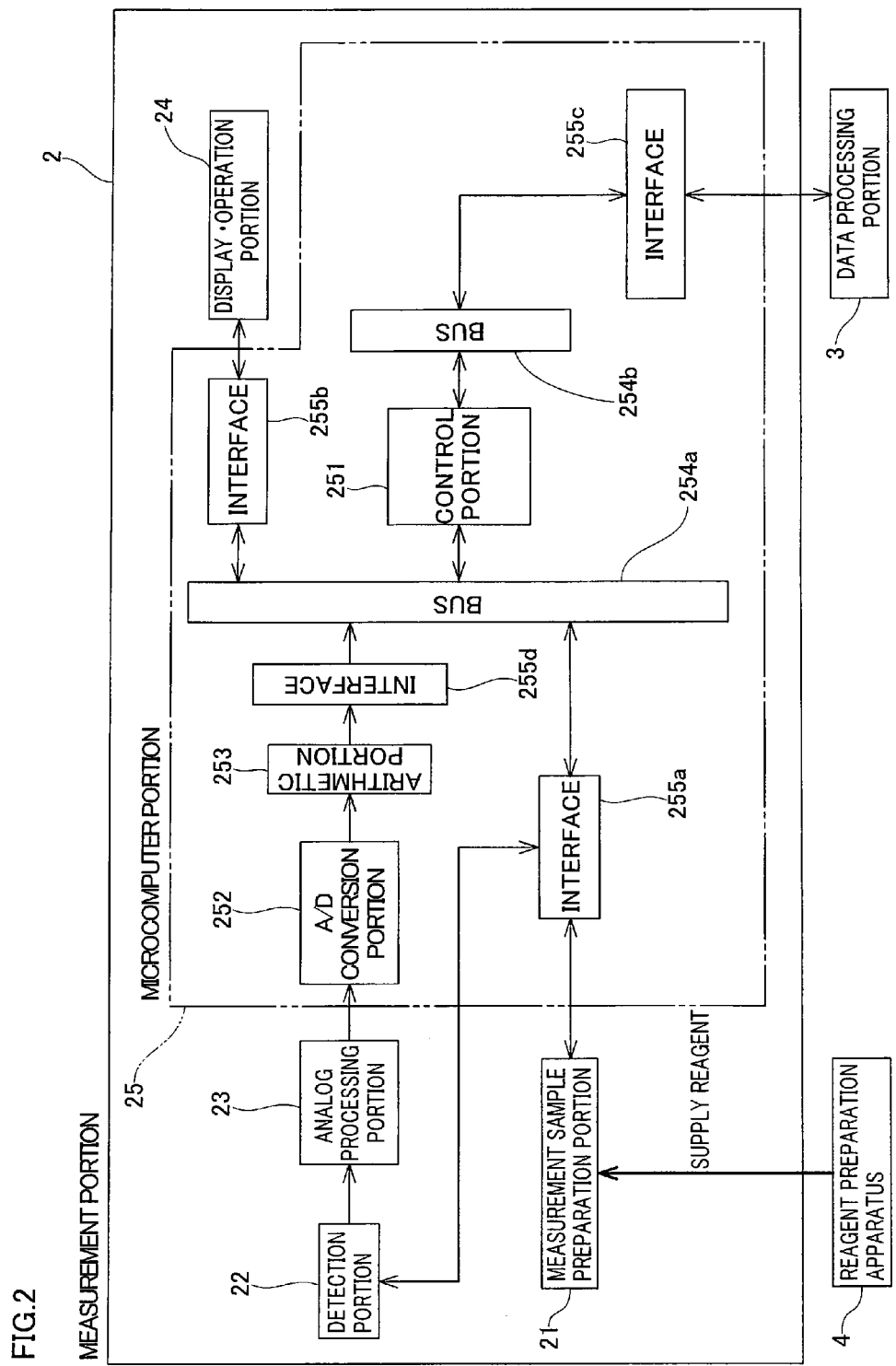
FIG. 2 is a block diagram showing the structure of a hemanalyzer including the reagent preparation apparatus according to the first embodiment shown in FIG. 1.

The measurement portion 2 includes a measurement sample preparation portion 21, the detection portion 22 performing measurement of the measurement sample, an analog processing portion 23 with respect to an output of the detection portion 22, a display•operation portion 24 and a microcomputer portion 25 for controlling the measurement portion 2, as shown in FIG. 2.

Figure 3:
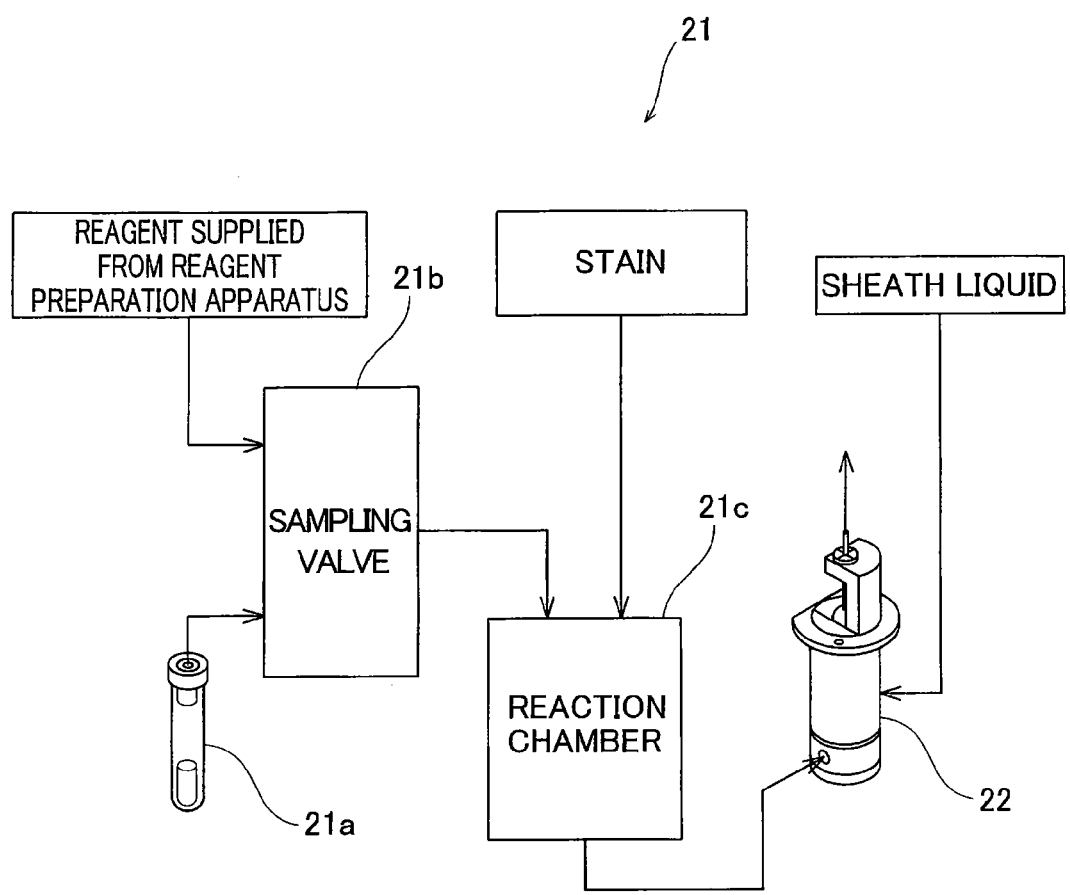
FIG. 3 is a diagram for illustrating a specimen preparation portion of the hemanalyzer including the reagent preparation apparatus according to the first embodiment shown in FIG. 1.

The measurement sample preparation portion 21 is provided for preparing a leukocyte measurement sample, a reticulocyte measurement sample and a platelet measurement sample. The measurement sample preparation portion 21 includes the sampling valve 21b by which the blood is sucked and the reaction chamber 21c, as shown in FIG. 3. A blood collection tube 21a stores the blood to be analyzed.

The sampling valve 21b has a function of determining the blood in the blood collection tube 21a sucked by a suction pipette (not shown) by a predetermined volume. Further, the sampling valve 21b is formed to be capable of mixing a predetermined reagent into the sucked blood. In other words, the sampling valve 21b is formed to be capable of forming a diluted sample in which a predetermined volume of reagent supplied from the reagent preparation apparatus 4 is mixed into the blood of the predetermined volume.

The reaction chamber 21c is formed to further mix a predetermined stain into the diluted sample supplied from the sampling valve 21b and to react the same for a predetermined time. Thus, the measurement sample preparation portion 21 has a function of preparing the leukocyte measurement sample in which leukocytes are stained and erythrocytes are hemolyzed. Further, the measurement sample preparation portion 21 has a function of preparing the reticulocyte measurement sample in which reticulocytes are stained and preparing the platelet measurement sample in which platelets are stained.

The measurement sample preparation portion 21 is formed to supply the leukocyte measurement sample from the measurement sample preparation portion 21 to the sheath flow cell 22c (see FIG. 4) described later along with a sheath liquid in a leukocyte differential measurement ("DIFF measurement") mode. Further, the measurement sample preparation portion 21 is formed to supply the reticulocyte measurement sample from the measurement sample preparation portion 21 to the sheath flow cell 22c along with the sheath liquid in a reticulocyte measurement ("RET measurement") mode. In addition, the measurement sample preparation portion 21 is formed to supply the platelet measurement sample from the measurement sample preparation portion 21 to the sheath flow cell 22c along with the sheath liquid in a platelet measurement ("PLT measurement") mode.

Figure 4:
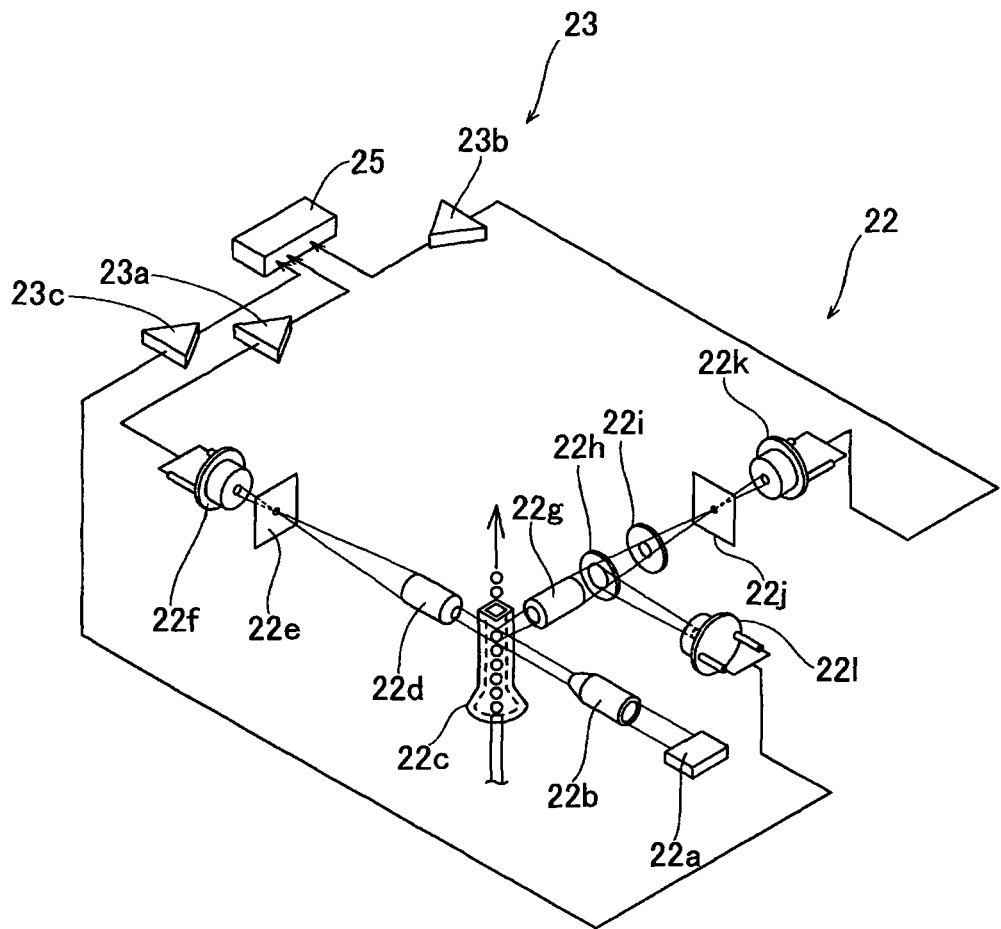
FIG. 4 is a schematic diagram showing a detection portion of the hemanalyzer including the reagent preparation apparatus according to the first embodiment shown in FIG. 1.

The detection portion 22 includes a light-emitting portion 22a emitting a laser beam, an irradiation lens unit 22b, the sheath flow cell 22c irradiated with the laser beam, a condenser lens 22d, a pinhole 22e and a PD (photodiode) 22f arranged on an extension in a direction where the laser beam emitted from the light-emitting portion 22a advances, a condenser lens 22g, a dichroic mirror 22h, an optical filter 22i, a pinhole 22j and an APD (avalanche photodiode) 22k arranged in a direction intersecting with the direction where the laser beam emitted from the light-emitting portion 22a advances, and a PD 22l arranged on a side portion of the dichroic mirror 22h, as shown in FIG. 4.

The light-emitting portion 22a is provided for emitting light with respect to the sample stream containing the measurement sample passing through the inner portion of the sheath flow cell 22c. The irradiation lens unit 22b is provided to convert the light emitted from the light-emitting portion 22a to parallel light. The PD 22f is provided for receiving forward scattered light emitted from the sheath flow cell 22c. Information related to the sizes of particles (blood cells) in the measurement sample can be obtained with the forward scattered light emitted from the sheath flow cell 22c.

The dichroic mirror 22h is provided for separating lateral scattered light and lateral fluorescence emitted from the sheath flow cell 22c from each other. More specifically, the dichroic mirror 22h is provided for introducing the lateral scattered light emitted from the sheath flow cell 22c into the PD 22l and introducing the lateral fluorescence emitted from the sheath flow cell 22c into the APD 22k. The PD 22l is provided for receiving the lateral scattered light. Internal information such as the sizes of nuclei of particles (blood cells) in the measurement sample can be obtained with the lateral scattered light emitted from the sheath flow cell 22c. The APD 22k is provided for receiving the lateral fluorescence. Information related to the degree of staining of the particles (blood cells) in the measurement sample can be obtained with the lateral fluorescence emitted from the sheath flow cell 22c. The PDs 22f and 22l and the APD 22k have functions of converting received optical signals to electric signals respectively.

The analog processing portion 23 includes amplifiers 23a, 23b and 23c, as shown in FIG. 4. The amplifiers 23a, 23b and 23c are provided for amplifying and waveform-processing the electric signals output from the PDs 22f and 22l and the APD 22k respectively.

The microcomputer portion 25 includes a control portion 251 having a control processor and a memory for operating the control processor, an A/D conversion portion 252 converting a signal output from the analog processing portion 23 to a digital signal and an arithmetic portion 253 for performing predetermined processing on the digital signal output from the A/D conversion portion 252, as shown in FIG. 2.

The control portion 251 has a function of controlling the measurement sample preparation portion 21 and the detection portion 22 through a bus 254a and an interface 255a. Further, the control portion 251 is connected with the display·operation portion 24 through the bus 254a and an interface 255b, and connected with the data processing portion 3 through a bus 254b and an interface 255c. The arithmetic portion 253 has a function of outputting an arithmetic result to the control portion 251 through an interface 255d and the bus 254a. The control portion 251 has a function of transmitting the arithmetic result (measurement data) to the data processing portion 3.

Figure 5:
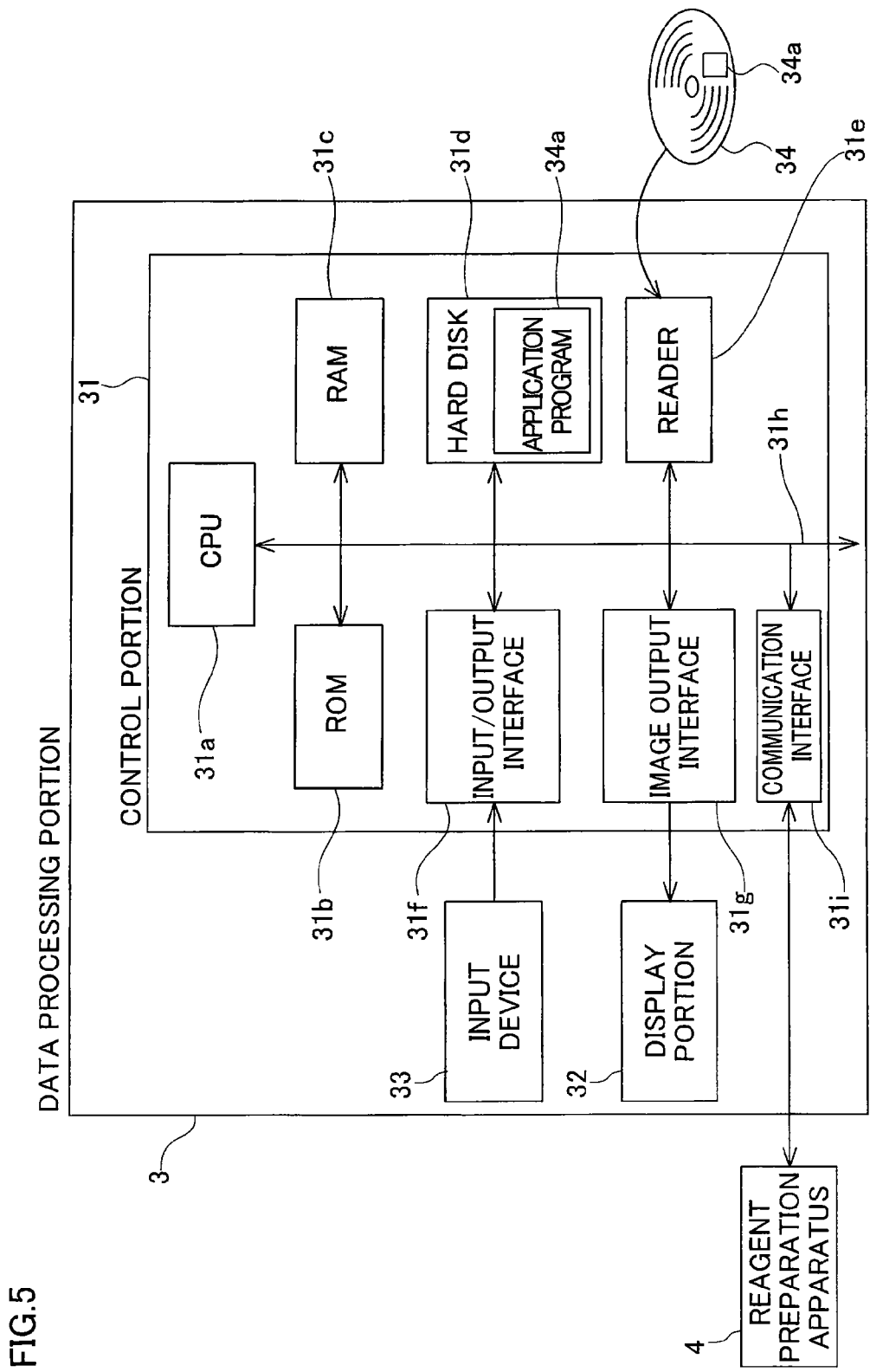
FIG. 5 is a block diagram showing the structure of a data processing portion of the hemanalyzer including the reagent preparation apparatus according to the first embodiment shown in FIG. 1.

The data processing portion 3 consists of a personal computer (PC) or the like as shown in FIG. 1, and has a function of analyzing the measurement data of the measurement portion 2 and displaying the analytical result thereof. The data processing portion 3 includes a control portion 31, a display portion 32 and an input device 33, as shown in FIG. 5.

The control portion 31 has a function of transmitting a measurement start signal including measurement mode information and a shutdown signal to the measurement portion 2. The control portion 31 is constituted of a CPU 31a, a ROM 31b, a RAM 31c, a hard disk 31d, a reader 31e, an input/output interface 31f, an image output interface 31g and a communication interface 31i, as shown in FIG. 5. The CPU 31a, the ROM 31b, the RAM 31c, the hard disk 31d, the reader 31e, the input/output interface 31f, the image output interface 31g and the communication interface 31i are connected with each other by a bus 31h.

The CPU 31a is provided for running computer programs stored in the ROM 31b and computer programs loaded in the RAM 31c. The ROM 31b is constituted of a mask ROM, a PROM, an EPROM, an EEPROM or the like, in which the computer programs run by the CPU 31a and data employed therefor are recorded.

The RAM 31c is constituted of an SRAM or a DRAM. The RAM 31c is employed for reading computer programs recorded in the ROM 31b and the hard disk 31d. Further, the RAM 31c is utilized as a working area of the CPU 31a when the CPU 31a runs these programs.

Various computer programs such as an operating system and application programs to be run by the CPU 31a and data employed for running the computer programs are installed in the hard disk 31d. An application program 34a described later is also installed in this hard disk 31d.

The reader 31e is constituted of a flexible disk drive, a CD-ROM drive or a DVD-ROM drive, and can read computer programs or data recorded in a portable recording medium 34. The application program 34a for making the computer implement predetermined functions is stored in the portable recording medium 34. The computer as the data processing portion 3 is formed to read the application program 34a from the portable recording medium 34 and to install the application program 34a in the hard disk 31d. An analysis program analyzing the specimen measured in the measurement portion and outputting the result of the analysis as the analytical result of the specimen can be cited as the application program 34a. Software having a function as a clock can also be cited as the application program 34a, and the analysis program associates the measurement time for the specimen with the analytical result and outputs the same.

The aforementioned application program 34a is not only provided by the portable recording medium 34, but can also be provided from an external apparatus communicably connected with the data processing portion 3 by an electric communication line (regardless of wired or wireless) through the aforementioned electric communication line. For example, it is also possible that the aforementioned application program 34a is stored in a hard disk of a server computer on the Internet and the data processing portion 3 accesses this server computer to download the application program 34a and to install the same in the hard disk 31d.

An operating system, such as Windows (registered trademark) manufactured and sold by Microsoft Corp. U.S.A., for example, providing a graphical user interface environment is installed in the hard disk 31d. In the following description, it is assumed that the application program 34a according to the first embodiment operates on the aforementioned operating system.

The input/output interface 31f is constituted of a serial interface such as USB, IEEE1394 or RS-232C, a parallel interface such as SCSI, IDE or IEEE1284, and an analog interface consisting of a D/A converter or an A/D converter, for example. The input device 33 consisting of a keyboard and a mouse is connected to the input/output interface 31f, and the user can input data in the data processing portion 3 by using the input device 33. Further, the user can select a measurement mode and start or shut down the measurement portion 2 by employing the input device 33.

The image output interface 31g is connected to the display portion 32 constituted of an LCD or a CRT, to output an image signal responsive to image data supplied from the CPU 31a to the display portion 32. The display portion 32 displays images (screen) according to the received image signal.

The reagent preparation apparatus 4 is provided for preparing a reagent employed in the measurement sample preparation portion 21 of the measurement portion 2. More specifically, the reagent preparation apparatus 4 is formed to prepare a reagent employed for hemanalysis by diluting a high-concentration reagent to a desired concentration with RO water prepared by an externally provided RO water preparation portion 7. The RO water is a kind of pure water, i.e., water from which impurities have been removed by being transmitted through an RO (Reverse Osmosis) membrane (reverse osmosis membrane). While the pure water includes purified water, deionized water and distilled water in addition to the RO water and is water on which processing of removing impurities has been executed, the purity thereof is not particularly restricted. The high-concentration reagent is a undiluted reagent in which concentrations of contained components are higher than those in the reagent supplied to the measurement portion 2.

Figure 6:
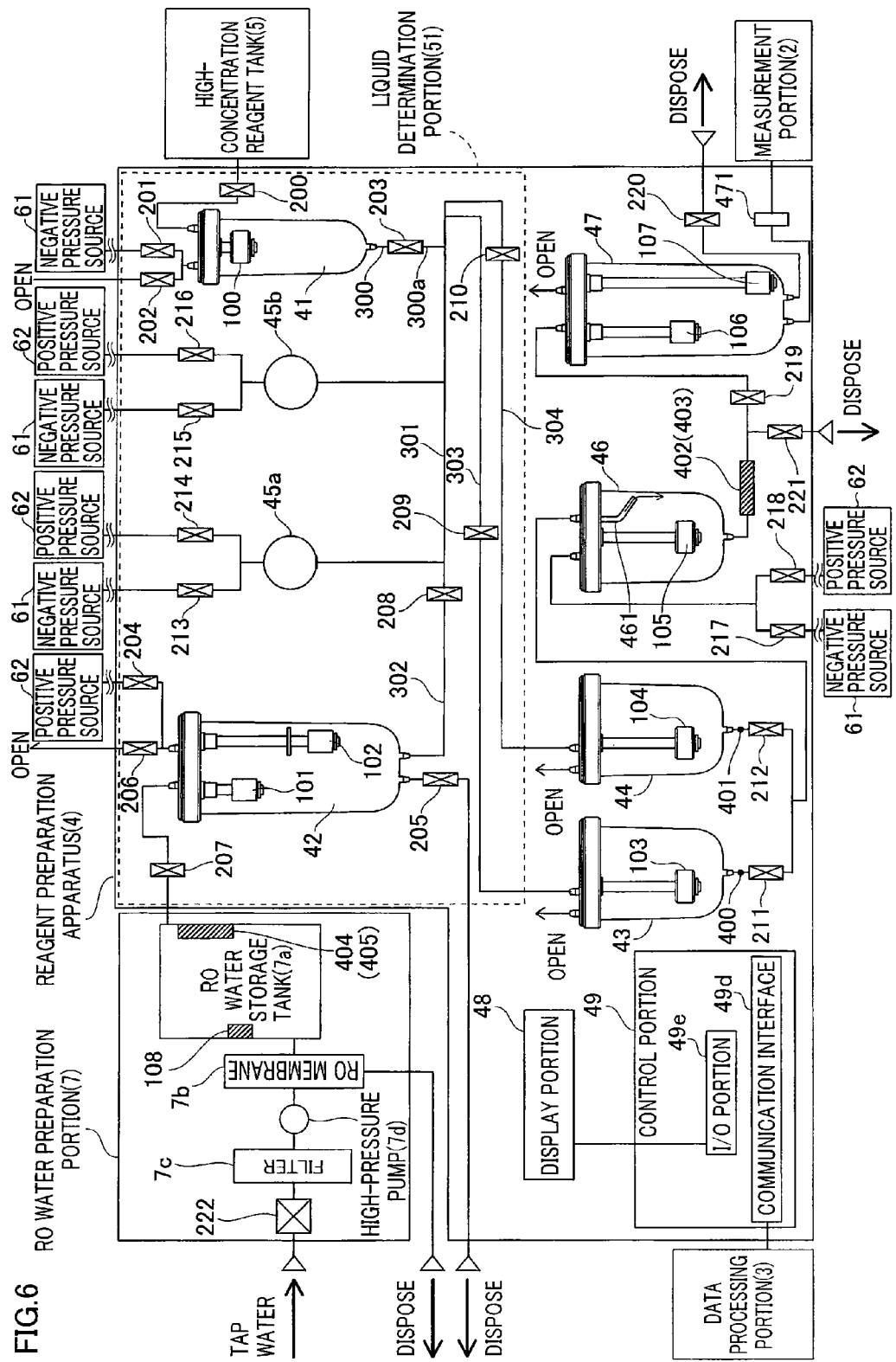
FIG. 6 is a schematic diagram showing the structure of the reagent preparation apparatus according to the first embodiment shown in FIG. 1.

The reagent preparation apparatus 4 includes a high-concentration reagent chamber 41, an RO water chamber 42, two dilution chambers 43 and 44, two diaphragm pumps 45a and 45b, a stirring chamber 46, a supply chamber 47, a display portion 48, a control portion 49 controlling operations of the respective portions of the reagent preparation apparatus 4 and a bar code reader 50 (see FIG. 1), as shown in FIG. 6. Further, the reagent preparation apparatus 4 includes a pneumatic portion 6 (see FIG. 1) set outside a housing, and is formed to transport respective liquids in the apparatus with negative pressure and positive pressure supplied from the pneumatic portion 6. The pneumatic portion 6 has negative pressure sources 61 for supplying the negative pressure to the reagent preparation apparatus 4 and positive pressure sources 62 for supplying the positive pressure.

The high-concentration reagent chamber 41 is so formed that the high-concentration reagent is supplied thereto from the high-concentration reagent tank 5. The high-concentration reagent chamber 41 is provided with a float switch 100 for sensing that a predetermined volume of the high-concentration reagent is stored in the chamber. The float switch 100 is so formed that a float portion vertically moves in response to the liquid volume (liquid level) in the high-concentration reagent chamber 41. The apparatus is so formed that the respective portions are controlled by the control portion 49 so that the high-concentration reagent is supplied from the high-concentration reagent tank 5 to the high-concentration reagent chamber 41 when the float portion of the float switch 100 reaches the lower limit. Further, the apparatus is so formed that the respective portions are controlled by the control portion 49 so that the supply of the high-concentration reagent from the high-concentration reagent tank 5 to the high-concentration reagent chamber 41 is stopped when the float portion 100 reaches the upper limit. The float switch 100 is arranged in the vicinity of an upper end portion of the high-concentration reagent chamber 41, and so formed that the float portion reaches the upper limit when the high-concentration reagent of about 300 mL is stored in the high-concentration reagent chamber 41. Thus, the high-concentration reagent is supplied to the high-concentration reagent chamber 41 to be regularly stored by about 300 mL.

The high-concentration reagent chamber 41 is connected to the high-concentration reagent tank 5 through an electromagnetic valve 200, and connected to the corresponding negative pressure source 61 of the pneumatic portion 6 through an electromagnetic valve 201. Further, the high-concentration reagent chamber 41 is formed to be opened to the atmosphere or blocked by opening/closing of an electromagnetic valve 202. In addition, the high-concentration reagent chamber 41 is connected to a channel 301 for transporting liquids from the diaphragm pump 45a (45b) to the dilution chamber 43 (44) by a channel 300. An electromagnetic valve 203 is provided on the channel 300, and the electromagnetic valve 203 is arranged in the vicinity of the channel 301. More specifically, the length of a channel 300a between the electromagnetic valve 203 and the channel 301 is set to a small value of about 15 mm. The channel 300 (300a) connected to the high-concentration reagent chamber 41 has an inner diameter of about 1.8 mm, while the channel 301 has an inner diameter of about 4.0 mm.

The RO water chamber 42 is so formed that the RO water for diluting the high-concentration reagent is supplied thereto from the RO water preparation portion 7. The RO water chamber 42 is provided with float switches 101 and 102 for sensing that the RO water stored in the chamber has reached the upper limit volume and that the same has reached the lower limit volume respectively. The float switch 101 (102) is so formed that a float portion vertically moves in response to the liquid volume (liquid level) in the RO water chamber 42. The apparatus is so formed that the respective portions are controlled by the control portion 49 so that the supply of the RO water from the RO water preparation portion 7 to the RO water chamber 42 is stopped when the float portion of the float switch 101 reaches a position corresponding to the upper limit volume of the RO water chamber 42. Further, the apparatus is so formed that the respective portions are controlled by the control portion 49 so that the RO water is supplied from the RO water preparation portion 7 to the RO water chamber 42 when the float portion of the float switch 102 reaches a position corresponding to the lower limit volume of the RO water chamber 42.

The float switch 101 is arranged in the vicinity of an upper end portion of the RO water chamber 42, and so formed that the float portion reaches the position corresponding to the upper limit volume of the RO water chamber 42 when the RO water of about 600 mL is stored in the Ro water chamber 42. The float switch 102 is so formed that the float portion reaches the position corresponding to the lower limit volume of the RO water chamber 42 when the RO water stored in the Ro water chamber 42 decreases to about 300 mL. Thus, it follows that the RO water of at least about 300 mL and not more than about 600 mL is stored in the RO water chamber 42 while the reagent preparation apparatus 4 operates.

The RO water chamber 42 is so formed that the RO water can be disposed from the chamber. More specifically, the RO water chamber 42 is connected to the corresponding positive pressure source 62 through an electromagnetic valve 204 and connected to a disposal channel through an electromagnetic valve 205, and so formed that the internal RO water is extruded into the disposal channel by positive pressure force by opening both of the electromagnetic valves 204 and 205. The RO water chamber 42 is formed to be opened to the atmosphere or blocked by opening/closing of an electromagnetic valve 206. Further, the RO water chamber 42 is connected to an RO water storage tank 7a, described later, of the RO water preparation portion 7 through an electromagnetic valve 207. In addition, the RO water chamber 42 is connected to the diaphragm pumps 45a and 45b by a channel 302 through an electromagnetic valve 208.

The dilution chambers 43 and 44 are provided for diluting the high-concentration reagent with the RO water. The dilution chamber 43 (44) is formed to be capable of storing a liquid (mixed liquid of the high-concentration reagent and the RO water) of about 300 mL delivered by the diaphragm pumps 45a and 45b, as described later. The dilution chamber 43 (44) is provided with a float switch 103 (104) for sensing that the residue of the liquid (mixed liquid of the high-concentration reagent and the RO water) stored in the chamber has reached a predetermined volume. The float switch 103 (104) is so formed that a float portion vertically moves in response to the liquid volume (liquid level) in the dilution chamber 43 (44). The dilution chamber 43 (44) is formed to be regularly in a state opened to the atmosphere. Further, the dilution chamber 43 (44) is connected to the channel 301 by a channel 303 (304) through an electromagnetic valve 209 (210). The channel 303 (304) has an inner diameter of about 4 mm, similarly to the channel 301. The liquids (the RO water and the high-concentration reagent) transported through the channel 301 can be transported to the dilution chamber 43 by opening the electromagnetic valve 209 in a state closing the electromagnetic valve 210. When opening the electromagnetic valve 210 in a state closing the electromagnetic valve 209, on the other hand, liquids (the RO water and the high-concentration reagent) transported through the channel 301 can be transported to the dilution chamber 44. In other words, the electromagnetic valves 209 and 210 are formed to function as channel switching portions for the channels 303 and 304 respectively.

The dilution chamber 43 (44) is connected to the stirring chamber 46 through an electromagnetic valve 211 (212). A bubble sensor 400 (401) is provided between the dilution chamber 43 (44) and the electromagnetic valve 211 (212). The bubble sensor 400 (401) is a transmission sensor, and formed to sense bubbles passing through a channel. Thus, the float portion of the float switch 103 (104) and bubbles are sensed by the bubble sensor 400 (401), so that it becomes possible to confirm that the liquid (mixed liquid of the high-concentration reagent and the RO water) in the dilution chamber 43 (44) has been entirely discharged by the control portion 49. The apparatus is so formed that the respective portions are controlled by the control portion 49 so that, when the dilution chamber 43 (44) is evacuated (the liquid in the chamber is entirely discharged), the high-concentration reagent and the RO water are supplied to the evacuated dilution chamber 43 (44).

The diaphragm pumps 45a and 45b have structures similar to each other, and are formed to simultaneously perform the same operation. The diaphragm pump 45a (45b) has a function of determining each of the high-concentration reagent and the Ro water by about 60 mL (constant volume) in a single determination operation. The diaphragm pump 45a (45b) is connected to the corresponding negative pressure source 61 through an electromagnetic valve 213 (215), and connected to the corresponding positive pressure source 62 through an electromagnetic valve 214 (216). A liquid determination portion 51 (see FIG. 6) of the reagent preparation apparatus 4 is constituted of the high-concentration reagent chamber 41, the RO water chamber 42, the diaphragm pumps 45a and 45b, the pneumatic portion 6, the channels 300 to 304 and the electromagnetic valves 200 to 210 and 213 to 216.

The stirring chamber 46 is formed to be capable of storing a liquid of about 300 mL and provided for stirring the liquid (mixed liquid of the high-concentration reagent and the RO water) transported from the dilution chamber 43 (44), as shown in FIG. 6. More specifically, the stirring chamber 46 has a bent pipe 416, and is so formed that the liquid (mixed liquid of the high-concentration reagent and the RO water) transported from the dilution chamber 43 (44) passes through the pipe 416, to be introduced into the stirring chamber 46 along the inner wall surface of the stirring chamber 46. Thus, the liquid (mixed liquid of the high-concentration reagent and the RO water) transported from the dilution chamber 43 (44) is flown along the inner wall surface of the stirring chamber 46, whereby the high-concentration reagent and the Ro water are easily stirred. While the high-concentration reagent and the Ro water are stirred to some extent also in the dilution chamber 43 (44) and in the channel from the dilution chamber 43 (44) to the stirring chamber 46, it is possible to more reliably stir the same by forming the stirring chamber 46 in the aforementioned manner.

The stirring chamber 46 is provided with a float switch 105 for sensing that the residue of the liquid (mixed liquid of the high-concentration reagent and the RO water) stored in the chamber has reached the predetermined volume. The float switch 105 is so formed that a float portion vertically moves in response to the liquid volume (liquid level) in the stirring chamber 46. The apparatus is so formed that the respective portions are controlled by the control portion 49 so that the mixed liquid of about 300 mL is supplied from either one of the stirring chambers 43 and 44 into the stirring chamber 46 when the float portion of the float switch 105 reaches the lower limit and the chamber is evacuated. When the mixed liquid supplied from either one of the dilution chambers 43 and 44 and stirred is discharged from the stirring chamber 46, the mixed liquid of about 300 mL is subsequently supplied from the other one of the dilution chambers 43 and 44 into the stirring chamber 46. The stirring chamber 46 is connected to the corresponding negative pressure source 61 through an electromagnetic valve 217, and connected to the corresponding positive pressure source 62 through an electromagnetic valve 218.

The supply chamber 47 is provided for storing the reagent of the predetermined volume to be supplied to the measurement portion 2. The supply chamber 47 has a storage volume of about 600 mL. The supply chamber 47 is provided with a float switch 106 for sensing that the residue of the reagent stored in the chamber has reached about 300 mL. The supply chamber 47 is further provided with a float switch 107 for sensing that the residue of the reagent stored in the supply chamber 47 has substantially reached zero. The float switch 106 (107) is so formed that a float portion vertically moves in response to the liquid volume (liquid level) in the supply chamber 47. The float portion of the float switch 106 is formed to be movable from the vicinity of an upper end portion to an intermediate position of the supply chamber 47 in the height direction. The apparatus is so formed that the respective portions are controlled by the control portion 49 so that the reagent of a desired concentration of about 300 mL is supplied from the stirring chamber 46 to the supply chamber 47 when the float portion of the float switch 106 reaches the intermediate position (lower limit position in the movable range of the float portion of the float switch 106) of the supply chamber 47 in the height direction. Thus, it follows that the reagent of the desired concentration of at least about 300 mL and not more than about 600 mL is regularly stored in the supply chamber 47. It is possible to quickly transport the reagent to the measurement portion 2 in response to a supply instruction by storing the reagent of the predetermined volume in the supply chamber 47 in this manner.

The float portion of the float switch 107 is formed to be movable in the vicinity of the bottom portion of the supply chamber 47. In a case where it is sensed by the float switch 107 that the residue of the reagent stored in the chamber has substantially reached zero, the supply of the reagent to the measurement portion 2 is stopped. Thus, even if the reagent has not been transported to the supply chamber 47 for some reason, it is possible to prevent bubbles from contaminating the reagent supplied to the measurement portion 2 while continuing the supply of the reagent to the measurement portion 2 to the utmost.

The supply chamber 47 is connected to the stirring chamber 46 through an electromagnetic valve 219. The supply chamber 47 is so formed that the reagent can be disposed from the chamber in maintenance or the like by opening an electronic valve 220. Further, the supply chamber 47 is formed to be regularly in a state opened to the atmosphere. In addition, the supply chamber 47 is connected to the measurement portion 2 through a filter 471. The filter 471 is provided for preventing impurities from contaminating the reagent supplied to the measurement portion 2.

A conductivity sensor 402 for measuring electric conductivity of the reagent is provided between the stirring chamber 46 and the supply chamber 47. The conductivity sensor 402 includes a temperature sensor 403 for measuring the temperature of the reagent on a position where the conductivity sensor 402 is arranged. The electric conductivity is obtained on the basis of an AD value of reference voltage and an AD value of electrode voltage acquired by the conductivity sensor 402, and the temperature of the reagent is obtained on the basis of an AD value of thermistor voltage acquired by the temperature sensor 403. A disposal channel is connected between the conductivity sensor 402 and the electromagnetic valve 219 through an electromagnetic valve 221.

The display portion 48 is provided on the outer surface of the reagent preparation apparatus 4, as shown in FIG. 1. Further, the display portion 48 is constituted of a touch panel liquid crystal display.

Figure 7:
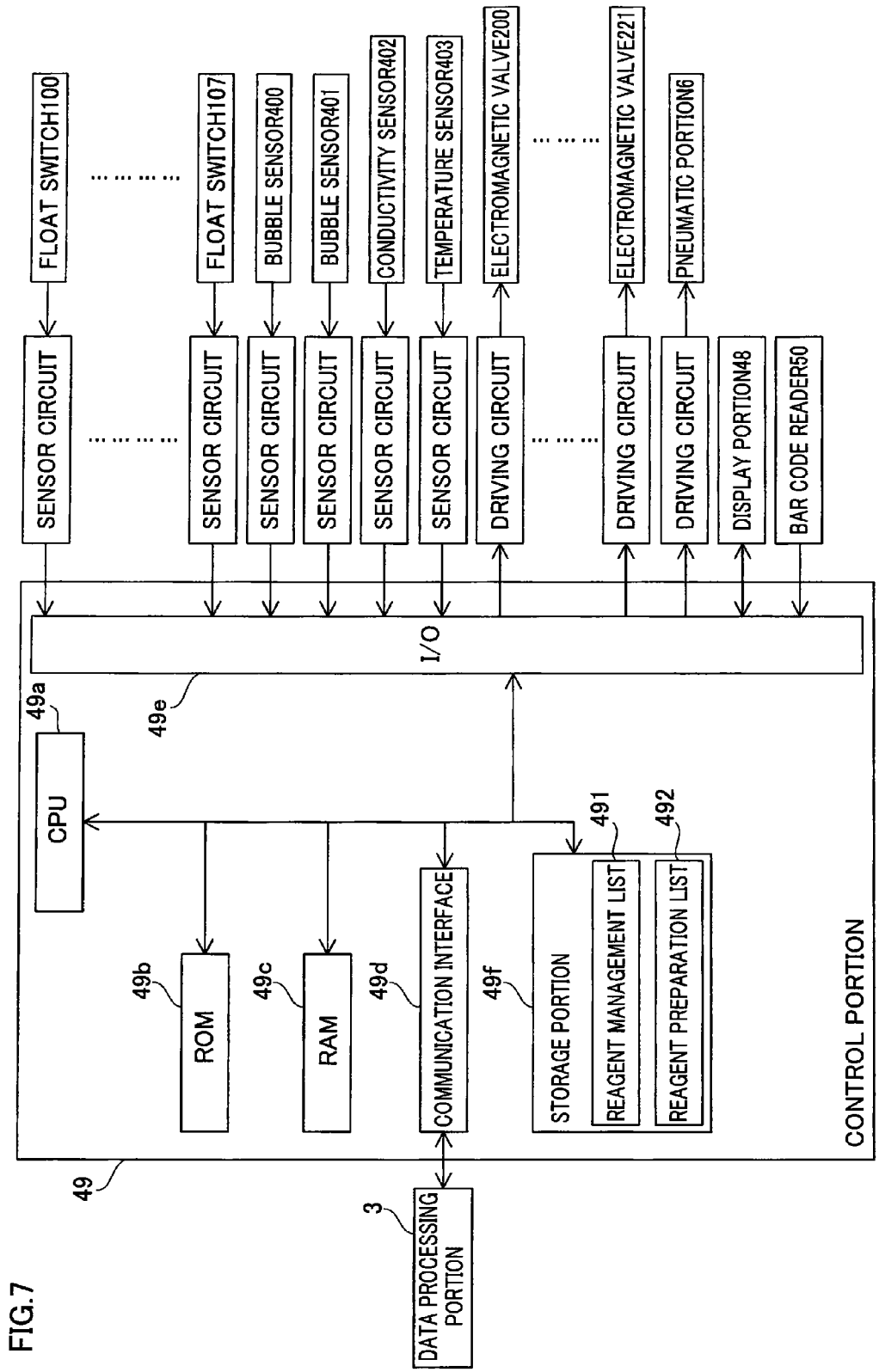
FIG. 7 is a block diagram for illustrating a control portion of the reagent preparation apparatus according to the first embodiment of the present invention.
Figure 8:
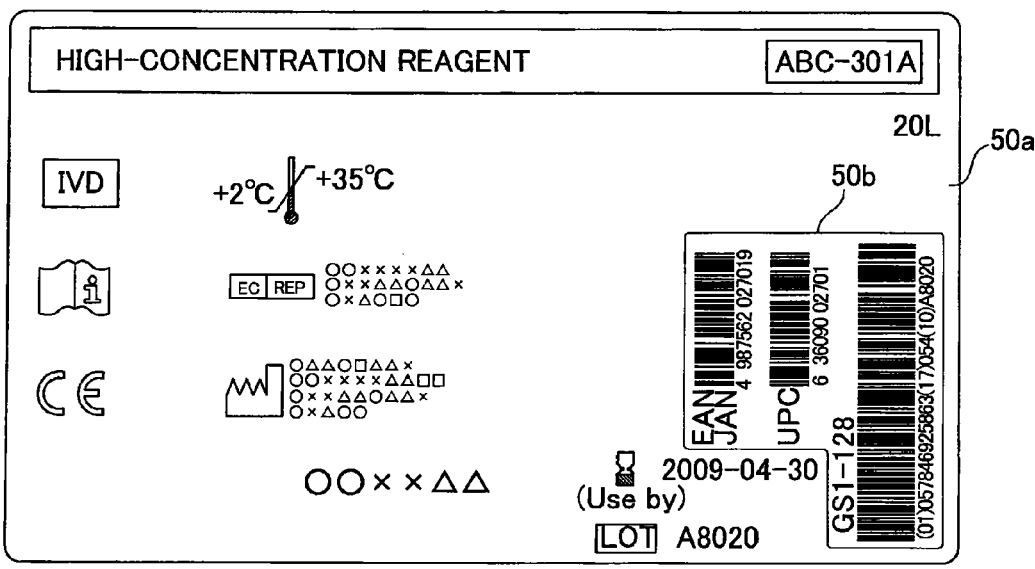
FIG. 8 is a diagram for illustrating a bar code reader of the reagent preparation apparatus according to the first embodiment of the present invention.

As shown in FIG. 7, the control portion 49 includes a CPU 49a, a ROM 49b, a RAM 49c, a communication interface 49d connected to the data processing portion 3, an I/O (Input/Output) portion 49e connected to the respective portions of the reagent preparation apparatus 4 and a storage portion 49f.

The CPU 49a is provided for running computer programs stored in the ROM 49b and computer programs loaded in the RAM 49c. The CPU 49a is formed to utilize the RAM 49c as a working area when running these computer programs. Software having a function as a clock can be cited as one of these computer programs. Dates described later are acquired by this software. A current time according to software of the reagent preparation apparatus 4 and a current time according to software of the data processing portion 3 are preferably rendered consistent with each other. Thus, association of the analytical result of the specimen and the supply time of the reagent can be more correctly performed.

A general formula for obtaining a target value of the electric conductivity of the reagent is shown in the following formula (1):

$$Z_0 = \{X + (A-1)Y\}/A \quad (1)$$

In the above formula (1), $Z_0$ represents a target value (ms/cm) of the electric conductivity of the reagent in which the high-concentration reagent and the RO water are mixed and stirred at 25° C., X represents the electric conductivity (Ms/cm) of the high-concentration reagent at 25° C., Y represents the electric conductivity (ms/cm) of the Ro water at 25° C., and A represents a dilution rate (known) (25 times in the first embodiment) respectively. X is a value specific to the high-concentration reagent, and a known value previously obtained by an experiment or the like.

A correction formula for taking into account the temperature of the RO water obtained by the temperature sensor 405 and the temperature of the reagent obtained by the temperature sensor 403 is shown in the following formula (2):

$$Z = [\{X + (A-1)Y\}/A] \times \{1 + \alpha 1(T2 - 25)\} \quad (2)$$
$$= [[X + (A-1)Y1/\{1 + \alpha 0(T1 - 25)\}]/A] \times$$
$$\{1 + \alpha 1(T2 - 25)\}$$

In the above formula (2), Z represents a target value (ms/cm) of the electric conductivity of the reagent in which the high-concentration reagent and the RO water are mixed and stirred at T2° C., Y1 represents the electric conductivity of the RO water at T1° C., T1 represents the temperature (° C.) of the RO water, T2 represents the temperature (° C.) of the reagent in which the high-concentration reagent and the RO water are mixed and stirred, $\alpha 0$ represents a temperature coefficient of the electric conductivity of the RO water with respect to 25° C., and $\alpha 1$ represents a temperature coefficient of the electric conductivity of the reagent in which the high-concentration reagent and the RO water are mixed and stirred with respect to 25° C. respectively. While the temperature coefficients $\alpha 0$ and $\alpha 1$ vary with the types of and the concentrations in the liquids, 0.02 is simply employed according to JIS (Japanese Industrial Standards).

The CPU 49a is formed to calculate the target value Z according to the aforementioned formula (2). Therefore, the CPU 49a decides the target value on the basis of the desired dilution rate A (known), the detected value Y1 of the electric conductivity of the RO water, the measured value T1 of the temperature of the RO water, the measured value T2 of the temperature of the mixed and stirred reagent and the electric conductivity X (known) of the high-concentration reagent.

According to the first embodiment, the CPU 49a is formed to make the storage portion 49f store reagent information such as a lot number, a post-preparation expiration date, a use start day and a post-opening expiration date of the high-concentration reagent. More specifically, a reagent management list 491 is stored in the storage portion 49f as described later, and the CPU 49a records the high-concentration reagent information in the reagent management list 491 on the basis of information read by the bar code reader 50.

Further, the CPU 49a is formed to make the storage portion 49f store reagent preparation history information including the date (reagent preparation date) when reagent preparation has been completed, electric conductivity at the time when the reagent preparation has been completed, the temperature at the time when the reagent preparation has been completed, an AD value (reference value) of reference voltage at the time when the reagent preparation has been completed, an AD value (electrode value) of electrode voltage at the time when the reagent preparation has been completed, an AD value (thermistor value) of thermistor voltage at the time when the reagent preparation has been completed, a reagent preparation result and a prepared reagent supply time zone. More specifically, a reagent preparation list 492 is stored in the storage portion 49f as described later, and the CPU 49a records the reagent preparation history information in the reagent preparation list 492 in reagent preparation processing, described later, shown in FIGS. 12 and 13. The aforementioned electric conductivity, the temperature, the AD value of the reference voltage, the AD value of the electrode voltage, the AD value of the thermistor voltage and the reagent reparation result are quality information indicating the quality of the prepared reagent.

The CPU 49a is formed to be capable of making the display portion 48 display various types of information (the high-concentration reagent information and the reagent preparation history information) recorded in the reagent management list 491 and the reagent preparation list 492 in response to an instruction from the user accepted through the touch panel display portion 48. Further, the CPU 49a is formed to accept a start instruction and a shutdown instruction for the reagent preparation apparatus 4 from the user through the touch panel display portion 48.

The communication interface 49d is formed to be capable of transmitting error information to the data processing portion 3 so that the user can confirm errors caused in the reagent preparation apparatus 4. As the error information, there is information for prompting the user to exchange the high-concentration reagent tank 5, information posting the user that the RO water has been unsupplied, information posting the user about abnormality of the negative pressure sources 61 and the positive pressure sources 62, or the like. An error notice is displayed on the display portion 48 on the basis of such error information.

The I/O portion 49e is so formed that signals are input therein from the float switches 100 to 107, the bubble sensors 400 and 401, the conductivity sensor 402 and the temperature sensor 403 through respective sensor circuits, as shown in FIG. 7. Further, the I/O portion 49e is formed to output signals to respective driving circuits in order to control driving of the electromagnetic valves 200 to 221 and the pneumatic portion 6 through the respective driving circuits. In addition, the I/O portion 49e is so formed that a signal responsive to an instruction of the user is input therein from the touch panel display portion 48, and formed to output an image signal such as image data to the display portion 48. Further, the I/O portion 49e is so formed that the information related to the high-concentration reagent read by the bar code reader 50 is input therein.

The storage portion 49f consists of a nonvolatile memory, and stores the reagent management list 491 and the reagent preparation list 492. The reagent management list 491 is formed to be rewritable by the CPU 49a, and capable of recording 100 high-concentration reagent data at the maximum. If the number of high-concentration reagent data exceeds 100, the high-concentration reagent data are successively overwritten from the oldest one. The reagent preparation list 492 is formed to be rewritable by the CPU 49a, and capable of recording 1000 reagent preparation history data at the maximum. If the number of reagent preparation history data exceeds 1000, the reagent preparation history data are successively overwritten from the oldest one.

The bar code reader 50 is a handheld one as shown in FIG. 1, and formed to be capable of reading bar codes 50b (see FIG. 8) of a label 50a stuck to the high-concentration reagent tank 5. The information such as the lot number of the high-concentration reagent and the post-preparation expiration date specific to each high-concentration reagent is included in the bar codes 50b.

The RO water preparation portion 7 is formed to be capable of preparing the RO water as a dilution liquid for diluting the high-concentration reagent with tap water. The RO water preparation portion 7 includes the RO water storage tank 7a, an RO membrane 7b and a filter 7c for protecting the RO membrane 7b by removing impurities contained in the tap water. Further, the RO water preparation portion 7 includes a high-pressure pump 7d applying high pressure to water passing through the filter 7c so that water molecules are transmitted through the RO membrane 7b and an electromagnetic valve 222 controlling supply of the tap water.

The RO water storage tank 7a is provided for storing the RO water transmitted through the RO membrane 7b. The RO water storage tank 7a is provided with a float switch 108 for sensing that RO water of a predetermined volume is stored therein. Further, the RO water storage tank 7a is provided with a conductivity sensor 404 for measuring the electric conductivity of the RO water in the RO water storage tank 7a. The conductivity sensor 404 includes a temperature sensor 405 for measuring the temperature of the RO water.

The RO water preparation portion 7 is formed to be capable of making the tap water reach the filter 7c by opening the electromagnetic valve 222. Further, the RO water preparation portion 7 is capable of transmitting the water passing through the filter 7c through the RO membrane 7b at high pressure by driving the high-pressure pump 7d. In addition, the RO water preparation portion 7 is formed to store the RO water of the predetermined volume in the RO water storage tank 7a on the basis of a sensing result of the float switch 108. The speed at which the RO water is supplied to the RO water storage tank 7a by the RO water preparation portion 7, i.e., the speed of preparation of the RO water by the RO water preparation portion 7 is at least about 20 L/hour and not more than not more than about 50 L/hour.

A high-concentration reagent information acquisition processing operation of the reagent preparation apparatus 4 according to the first embodiment of the present invention is now described with reference to FIGS. 8 to 11.

Figure 9:
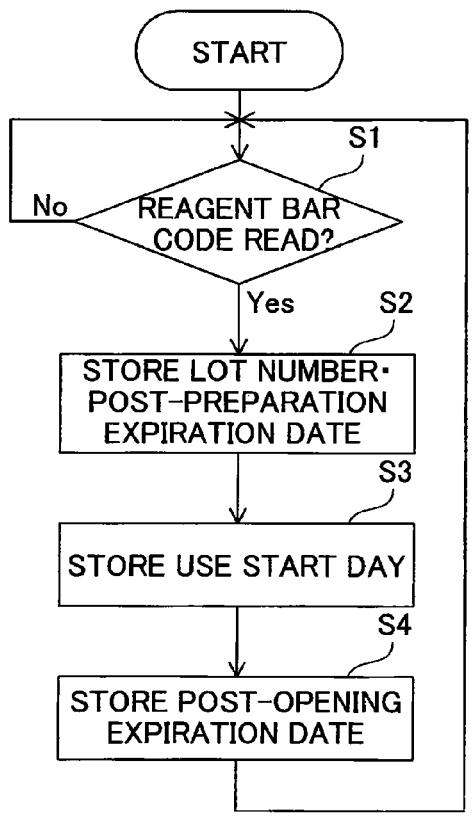
FIG. 9 is a flow chart for illustrating a high-concentration reagent information acquisition processing operation of the reagent preparation apparatus according to the first embodiment of the present invention.

First, whether or not the bar code reader 50 has read the bar codes 50b (see FIG. 8) of the label 50a stuck to the high-concentration reagent tank 5 is determined by the CPU 49a at a step S1 in FIG. 9. More specifically, when the user presses a reagent exchange button 481c of a menu screen 481 (see FIG. 10) displayed on the display portion 48, a reagent exchange screen 482 is displayed as shown in FIG. 11. Thereafter the user arranges the handheld bar code reader 50 on bar codes 50b (see FIG. 8) of a new high-concentration reagent tank 5, whereby the bar codes 50b are read by the bar code reader 50.

Figure 10:
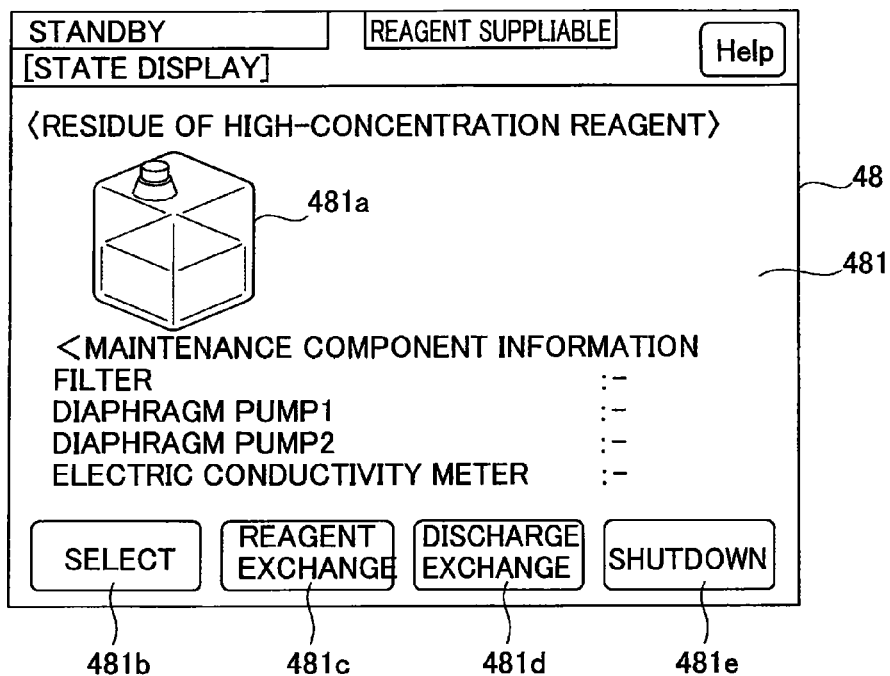
FIG. 10 is a screen diagram for illustrating the high-concentration reagent information acquisition processing operation of the reagent preparation apparatus according to the first embodiment of the present invention.
Figure 11:
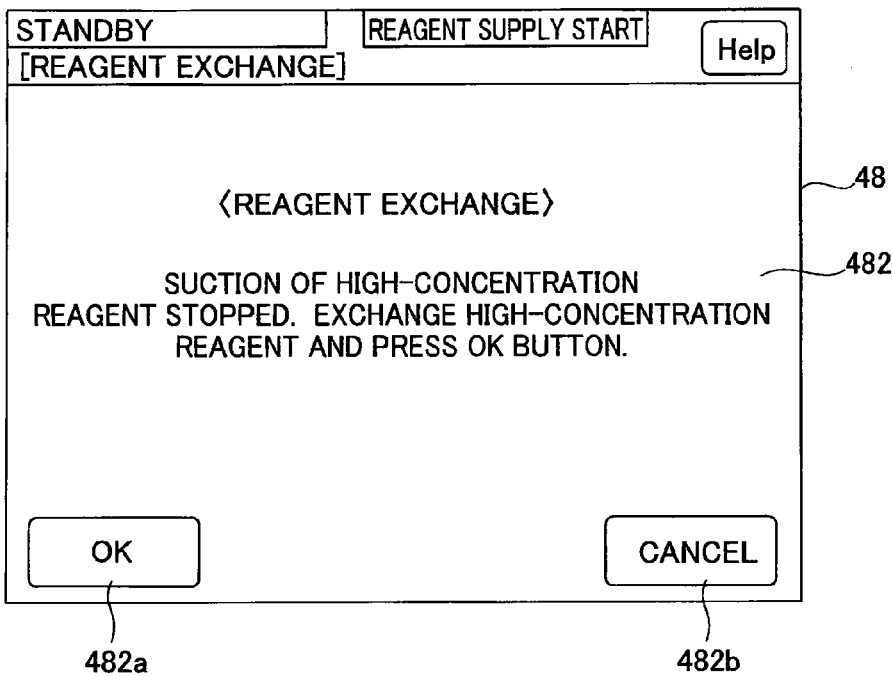
FIG. 11 is a screen diagram for illustrating the high-concentration reagent information acquisition processing operation of the reagent preparation apparatus according to the first embodiment of the present invention.

A schematic diagram 481a showing the residue of the high-concentration reagent, a select button 481b, the reagent exchange button 481c, a discharge exchange button 481d and a shutdown button 481e are displayed on the menu screen 481, as shown in FIG. 10. The select button 481b is pressed when the user confirms various settings and various items, as described later. The discharge exchange button 481d is pressed when the user exchanges a discharge tank (not shown) storing a discharge disposed from the reagent preparation apparatus 4. The shutdown button 481e is pressed when the user shuts down the reagent preparation apparatus 4. Contents of a purport of stopping suction of the high-concentration reagent and a purport of prompting the user to exchange the high-concentration reagent are displayed on the reagent exchange screen 482. Further, an OK button 482a and a cancel button 482b are displayed on the reagent exchange screen 482. The OK button 482a is pressed after exchange of the high-concentration reagent tank 5 is completed. The cancel button 482b is pressed when the user stops exchanging the high-concentration tank 5.

At the step S1, this determination is repeated until the bar codes 50b are read by the bar code reader 50. When the bar codes 50b are read, the lot number and the post-preparation expiration date of the high-concentration reagent are stored in the storage portion 49f on the basis of the bar codes 50b by the CPU 49a at a step S2. More specifically, the lot number and the post-preparation expiration date of a new high-concentration reagent are stored in the reagent management list 491 of the storage portion 49f.

Thereafter the CPU 49a makes the storage portion 49f store the day when the bar code reader 50 has read the bar codes 50b as the use start day of the high-concentration reagent at a step S3. In other words, the use start day of the high-concentration reagent is stored in the reagent management list 491 of the storage portion 49f. At a step S4, the CPU 49a makes the storage portion 49f store the post-opening expiration date of the high-concentration reagent. More specifically, the CPU 49a makes the storage portion 49f store a period of 30 days from the use start day (the day when the bar code reader 50 has read the bar codes 50b) of the high-concentration reagent as the post-opening expiration date. In other words, the post-opening expiration date of the high-concentration reagent is recorded in the reagent management list 491 of the storage portion 49f. The processing from the step S1 to the step S4 is repetitively executed from the start of the reagent preparation apparatus 4 until the same is shut down.

A reagent preparation processing operation of the reagent preparation apparatus 4 according to the first embodiment of the present invention is now described with reference to FIGS. 6 and 12 to 15.

Figure 12:
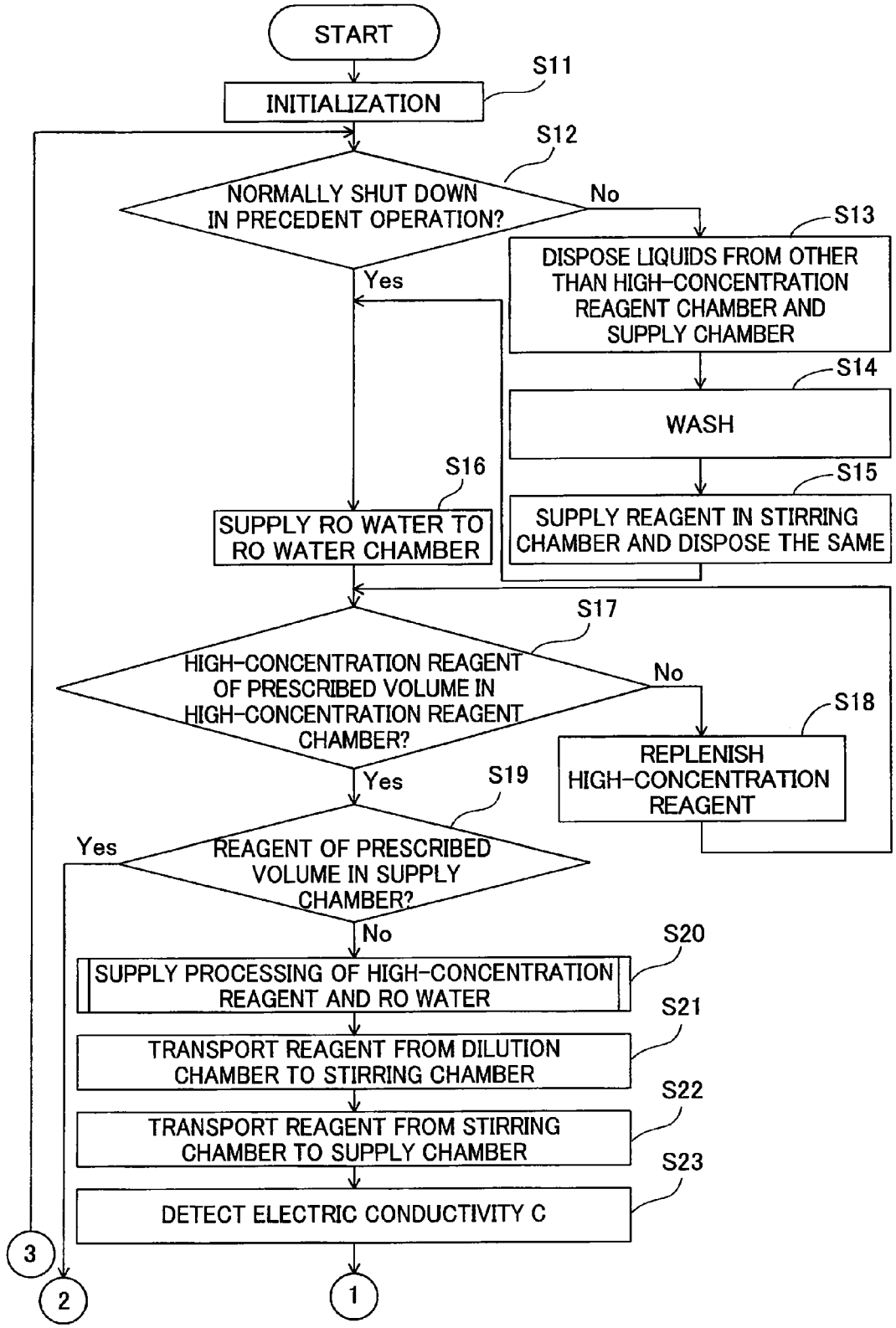
FIG. 12 is a flow chart for illustrating a reagent preparation processing operation of the reagent preparation apparatus according to the first embodiment of the present invention.

First, initialization of the corresponding computer program stored in the ROM 49b is performed by the CPU 49a at a step S11 in FIG. 12. Then, whether or not the reagent preparation apparatus 4 has been normally shut down in precedent operation completion is determined by the CPU 49a at a step S12. More specifically, it is determined on the basis of a flag set to ON in a case where the reagent preparation apparatus 4 has been normally shut down, as described later. The processing advances to a step S16 in the case where the reagent preparation apparatus 4 has been normally shut down, and advances to a step S13 in a case where the reagent preparation apparatus 4 has not been normally shut down.

At the step S13, the liquids in the chambers 42, 43, 44 and 46 other than the high-concentration reagent chamber 41 and the supply chamber 47 are entirely disposed. More specifically, the electromagnetic valves 204 and 205 are opened by the CPU 49a in a state closing the electromagnetic valves 206, 207 and 208, to dispose the RO water from the RO water chamber 42. The RO water disposed from the RO water chamber 42 may be transported to the RO water preparation portion 7 again, to prepare new RO water from the disposed RO water. Further, the electromagnetic valves 218 and 221 are opened by the CPU 49a in a state closing the electromagnetic valves 211, 212, 217 and 219, to extrude the mixed liquid from the stirring chamber 46 into the disposal channel with positive pressure force. In addition, the electromagnetic valves 211 and 217 are opened by the CPU 49a in a state closing the electromagnetic valves 212, 218, 219 and 221 to transport the mixed liquid from the dilution chamber 43 to the stirring chamber 46 with negative pressure force, and to thereafter dispose the mixed liquid from the stirring chamber 46 by the aforementioned operation. Also as to the mixed liquid in the dilution chamber 44, the electromagnetic valves 212 and 217 are opened by the CPU 49a in the state closing the electromagnetic valves 211, 218, 219 and 221, thereby transporting the same to the stirring chamber 46 with negative pressure force.

Thus, the liquids in the chambers 42, 43, 44 and 46 other than the high-concentration reagent chamber 41 and the supply chamber 47 are so entirely disposed at the step S13 that it is possible to prevent an operation of using RO water having a possibility of being retained for a long time for reagent preparation and an operation of forming a reagent whose dilution rate is unclear.

Thereafter washing of the channels, the RO water chamber 42, the dilution chamber 43 (44) and the stirring chamber 46 is performed at a step S14. More specifically, the electromagnetic valves 206, 208 and 213 (215) are opened by the CPU 49a after RO water newly prepared by the RO water preparation portion 7 is supplied to the RO water chamber 42, whereby RO water of about 12.0 mL (about 6.0 mL to each diaphragm pump) is introduced into the diaphragm pump 45a (45b) with negative pressure force. Then, the electromagnetic valves 214 (216) and 209 are opened in a state closing the electromagnetic valves 208 and 213 (215), thereby transporting the RO water of about 12.0 mL (about 6.0 mL in each diaphragm pump) in the diaphragm pump 45a (45b) to the dilution chamber 43 with positive pressure force. The aforementioned operation is repeated 25 times, whereby newly prepared RO water of about 300 mL is supplied to the dilution chamber 43.

Thereafter the electromagnetic valves 211 and 217 are opened by the CPU 49a, thereby transporting the RO water of about 300 mL from the dilution chamber 43 to the stirring chamber 46. Then, the electromagnetic valves 218 and 221 are opened by the CPU 49a in a state closing the electronic valves 217 and 219, thereby disposing the RO water from the stirring chamber 46.

While the RO water is transported from the dilution chamber 43 to the stirring chamber 46, newly prepared RO water of about 300 mL is supplied to the dilution chamber 44 by an operation similar to that of transporting the RO water to the dilution chamber 43. The transportation of the RO water from the dilution chamber 44 to the stirring chamber 46 is also performed by an operation similar to the transportation from the dilution chamber 43 to the stirring chamber 46. Thus, the inner portions of the respective ones of the channels, the RO water chamber 42, the dilution chamber 43 (44) and the stirring chamber 46 are washed with the newly prepared RO water by the aforementioned series of operations. In advance of the aforementioned step S13, RO water of the predetermined volume is already stored in the RO water chamber 42.

Then, a reagent is supplied in the stirring chamber 46 by an operation similar to the operation of forming the reagent of the desired concentration, and the supplied reagent is entirely disposed at a step S15. More specifically, the reagent of the desired concentration is supplied to the stirring chamber 46 by operations at steps S20 and S21 described later, and thereafter the electronic valves 218 and 221 are opened by the CPU 49a in a state closing the electromagnetic valves 217 and 219, thereby disposing the reagent from the stirring chamber 46. Thus, even if reagents of concentrations exceeding the desired concentration remain in the channels, the dilution chamber 43 (44) and the stirring chamber 46, the channels and the chambers are washed also by the reagent of the desired concentration in addition to the aforementioned washing with the RO water, whereby the reagent can be inhibited from being prepared in a concentration other than the desired concentration.

Then, RO water is supplied to the RO water chamber 42 at a step S16. Then, at a step S17, whether or not the high-concentration reagent of the predetermined volume is stored in the high-concentration reagent chamber 41 is determined by the CPU 49a on the basis of a sensing result of the float switch 100. If the high-concentration reagent of the predetermined volume is not stored, the high-concentration reagent is replenished from the high-concentration reagent tank 5 to the high-concentration reagent chamber 41 at a step S18. More specifically, the electromagnetic valves 200 and 201 are opened by the CPU 49a in a state closing the electromagnetic valves 202 and 203, thereby supplying the high-concentration reagent to the high-concentration reagent chamber 41 with negative pressure force.

If the high-concentration reagent of the predetermined volume is stored in the high-concentration reagent chamber 41, whether or not the reagent of the predetermined volume is stored in the supply chamber 47 is determined by the CPU 49a at a step S19. In other words, whether or not a reagent of at least about 300 mL and not more than 600 mL is stored in the supply chamber 47 is determined. If the reagent of the predetermined volume is stored, the processing is shifted to a step S30. If the reagent of the predetermined volume is not stored, on the other hand, supply processing of the high-concentration reagent and the RO water is performed at the step S20.

A supply processing operation of the high-concentration reagent and the RO water at the step S20 in the reagent preparation processing operation shown in FIG. 12 is now described with reference to FIGS. 6 and 14.

First, as an initial state (state immediately before the reagent preparation processing) of the reagent preparation apparatus 4, the channels 301 to 304 shown in FIG. 6 are substantially filled with the RO water, while the channel 300 is substantially filled with the high-concentration reagent. While the channel 300 and the channel 301 are directly connected with each other, the inner diameter of the channel 300 (300a) is small at about 1.8 mm with respect to the inner diameter of about 4.0 mm of the channel 301, and hence the high-concentration reagent in the channel 300 is hardly mixed with the RO water in the channel 301. Further, the channel 300a between the electromagnetic valve 203 and the channel 301 has the inner diameter of about 1.8 mm and is set to the small length of about 15 mm, and hence the volume of the high-concentration reagent present in the channel 300a is extremely small.

Figure 14:
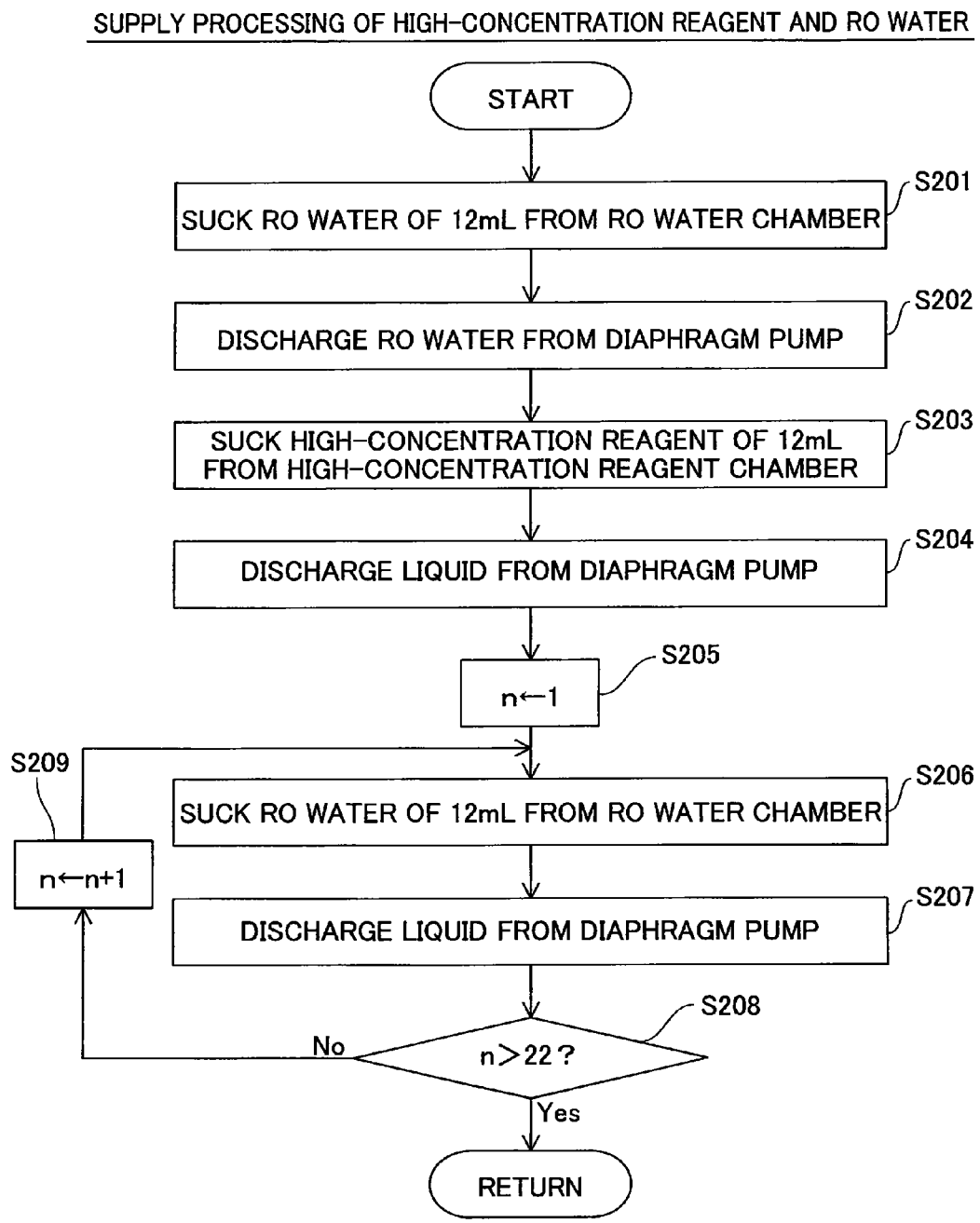
FIG. 14 is a flow chart for illustrating a supply processing operation for a high-concentration reagent and RO water at a step S20 in the reagent preparation processing operation shown in FIG. 12.

At a step S201 in FIG. 14, RO water of about 12.0 mL (about 6.0 mL in each diaphragm pump) is sucked from the RO water chamber 42 by the diaphragm pumps 45a and 45b. More specifically, the electromagnetic valves 213 (215) and 208 are opened by the CPU 49a, whereby the RO water is introduced into the diaphragm pump 45a (45b). Then, the electromagnetic valves 213 (215) and 208 are closed and thereafter the electromagnetic valves 214 (216) and 209 are opened at a step S202, whereby positive pressure is supplied to the diaphragm pump 45a (45b) and the RO water is discharged. Thus, RO water of about 12.0 mL (6.0 mL in each diaphragm pump) is supplied to the dilution chamber 43 through the channels 301 and 303.

Thereafter the high-concentration reagent of about 12.0 mL (6.0 mL in each diaphragm pump) is sucked from the high-concentration reagent chamber 41 by the diaphragm pumps 45a and 45b at a step S203. More specifically, the electromagnetic valves 214 (216) and 209 are closed and the electromagnetic valves 202, 203 and 213 (215) are thereafter opened by the CPU 49a, whereby negative pressure is supplied and the high-concentration reagent is sucked to the diaphragm pump 45a (45b). More detailedly, the high-concentration reagent of about 12.0 mL discharged from the high-concentration reagent chamber 41 is mixed with the RO water remaining in the channel 301, whereby a mixed liquid of the RO water and the high-concentration reagent is sucked to the diaphragm pump 45a (45b). At this time, the channel 301 is filled with the mixed liquid of the RO water and the high-concentration reagent. In other words, the high-concentration reagent of about 12.0 mL flown out of the high-concentration reagent chamber 41 is present in a region combining the diaphragm pump 45a (45b) and the channel 301 with each other. While the high-concentration reagent is present also in the channel 300a, the volume of the high-concentration reagent present in the channel 300a is extremely small as described above, and hence the same is substantially negligible. In suction of the high-concentration reagent after a second reagent preparation processing operation, the high-concentration reagent having remained in the channel 300a is extruded toward the side of the channel 301 by the precedent reagent preparation processing operation, whereby it follows that the high-concentration reagent of about 12.0 mL is more correctly present in the region combining the diaphragm pump 45a (45b) and the channel 301 with each other.

Then, the electromagnetic valves 202, 203 and 213 (215) are closed and the electromagnetic valves 214 (216) and 209 are thereafter opened at a step S204, whereby positive pressure is supplied and the mixed liquid of the RO water and the high-concentration reagent is discharged from the diaphragm pump 45a (45b). Thus, the mixed liquid of the RO water and the high-concentration reagent is supplied to the dilution chamber 43 through the channels 301 and 303. At this time, the high-concentration reagent of several mL remains in the channels 301 and 303 in a state mixed with the RO water.

At a step S205, n is set to 1 by the CPU 49a. Here, n represents a discharge frequency of the RO water by the diaphragm pumps 45a and 45b, and is defined by a real number starting from 1. Then, at a step S206, RO water of about 12.0 mL is sucked from the RO water chamber 42 by the diaphragm pumps 45a and 45b, similarly to the aforementioned step S201. At a step S207, the RO water is discharged from the diaphragm pumps 45a and 45b, similarly to the aforementioned step S202. Thus, the high-concentration reagents having remained in the channels 301 and 303 are transported to the dilution chamber 43 along with the RO water.

Thereafter whether or not n is greater than 22 is determined by the CPU 49a at a step S208. If n is not greater than 22, n is set to n+1 at a step S209, and the operations of the steps S206 to S209 are repeated until n becomes greater than 22. In other words, the operations at the steps S206 to S209 are repeated until the operation of sucking and discharging the RO water is performed 24 times with respect to one operation of sucking and discharging the high-concentration reagent by the diaphragm pumps 45a and 45b. When n becomes greater than 22, the operations are terminated. Thus, a mixed liquid of about 288 mL+about 12 mL=about 300 mL is supplied to the dilution chamber 43, with the RO water of about 12.0 mL×24 times=about 288 mL and the high-concentration reagent of about 12.0 mL×one time=about 12 mL. The operation of sucking and discharging the RO water is performed 23 times after the operation of sucking and discharging the high-concentration reagent by the diaphragm pumps 45a and 45b, whereby the high-concentration reagents having remained in the channels 301 and 303 are entirely transported to the dilution chamber 44, and the channels 301 and 303 consequently enter states where only the RO water is present therein.

When driving the electromagnetic valve 210 in place of the electromagnetic valve 209 in the aforementioned operations, it is possible to transport a mixed liquid of about 300 mL consisting of RO water of about 288 mL and a high-concentration reagent of about 12 mL to the dilution chamber 44.

After the supply processing of the high-concentration reagent and the RO water through the step S20 in FIG. 12 is performed, the electromagnetic valves 211 (212) and 217 are opened by the CPU 49a at a step S21, to transport the reagent from the dilution chamber 43 (44) to the stirring chamber 46 with negative pressure force. At this time, the transported reagent is flown by the pipe 416 provided in the stirring chamber 46 to be along the inner wall of the stirring chamber 46, thereby being stirred in the stirring chamber 46.

Then, at a step S22, the electromagnetic valves 211 (212) and 217 are closed and the electromagnetic valves 218 and 219 are thereafter opened, whereby the reagent is transported from the stirring chamber 46 to the supply chamber 47. At this time, the electric conductivity C is measured by the conductivity sensor 402 and the temperature T2 of the reagent is measured by the temperature sensor 403 at a step S23. In other words, the AD value of the reference voltage and the AD value of the electrode voltage are so detected that the electric conductivity C is acquired by the conductivity sensor 402. Further, the AD value of the thermistor voltage is so detected that the temperature T2 of the reagent is acquired by the temperature sensor 403.

At a step S24, the CPU 49a makes the storage portion 49f store the electric conductivity C and the temperature T2 of the reagent having currently passed through the conductivity sensor 402 and the temperature sensor 403, the AD value of the reference voltage, the AD value of the electrode voltage and the AD value of the thermistor voltage as the electric conductivity at the time when the reagent preparation has been completed, the temperature at the time when the reagent preparation has been completed, the reference value at the time when the reagent preparation has been completed, the electrode value at the time when the reagent preparation has been completed and the thermistor value at the time when the reagent preparation has been completed respectively. More specifically, the electric conductivity at the time when the reagent preparation has been completed, the temperature at the time when the reagent preparation has been completed, the reference value at the time when the reagent preparation has been completed, the electrode value at the time when the reagent preparation has been completed and the thermistor value at the time when the reagent preparation has been completed are recorded in the reagent preparation list 492 of the storage portion 49f by the CPU 49a. Further, the CPU 49a makes the storage portion 49f store the date when the reagent has passed the conductivity sensor 402 and the temperature sensor 403 as the current reagent preparation date. In other words, the current reagent preparation date is recorded in the reagent preparation list 492 of the storage portion 49f by the CPU 49a.

The date (date and time) when the reagent has passed through the conductivity sensor 402 and the temperature sensor 403 is the date (date and time) immediately before the reagent is supplied to the supply chamber 47, and the date (date and time) when the reagent has passed through the conductivity sensor 402 and the temperature sensor 403 and the date (date and time) when the reagent is supplied to the supply chamber 47 substantially coincide with each other. According to the first embodiment, therefore, the date (date and time) when the reagent has passed through the conductivity sensor 402 and the temperature sensor 403 is considered as the date (date and time) when the reagent is supplied to the supply chamber 47, and the date (date and time) when the reagent has passed through the conductivity sensor 402 and the temperature sensor 403, i.e., the date (date and time) when the reagent is supplied to the supply chamber 47 is regarded as the reagent preparation date.

Thereafter whether or not the electric conductivity C is within a predetermined range is determined by the CPU 49a at a step S25. More specifically, whether or not the measured electric conductivity C is within the predetermined range is determined with respect to the target value Z of the electric conductivity at the dilution rate of 25 times calculated according to the above formula (2). If the electric conductivity C is not within the predetermined range, it is recorded that the reagent preparation result is NG in the reagent preparation list 492 of the storage portion 49f by the CPU 49a at a step S26. Then, at a step S27, the electromagnetic valve 219 is closed while the electromagnetic valve 221 is opened, and the reagent whose electric conductivity C is not within the predetermined range is disposed through the disposal channel. Thus, it becomes possible to store only a precisely diluted reagent in the supply chamber 47.

If the electric conductivity C is within the predetermined range, on the other hand, it is recorded that the reagent preparation result is G (Good) in the reagent preparation list 492 of the storage portion 49f by the CPU 49a at a step S28. Then, at a step S29, the CPU 49a makes the storage portion 49f store the prepared reagent supply time zone of the reagent whose reagent preparation result has been recorded as G (Good) at the time before the precedent one. In other words, the prepared reagent supply time zone of the reagent whose reagent preparation result has been recorded as G (Good) at the time before the precedent one is recorded in the reagent preparation list 492 of the storage portion 49f.

The prepared reagent supply time zone is described with reference to FIG. 15. The prepared reagent supply time zone of the reagent is a time zone having a possibility that the corresponding reagent has been transported from the reagent preparation apparatus 4 to the measurement portion 2. Further, the prepared reagent supply time zone is acquired by the CPU 49a on the basis of a plurality of reagent preparation dates acquired every time the reagent passes through the conductivity sensor 402 and the temperature sensor 403.

Figure 15:
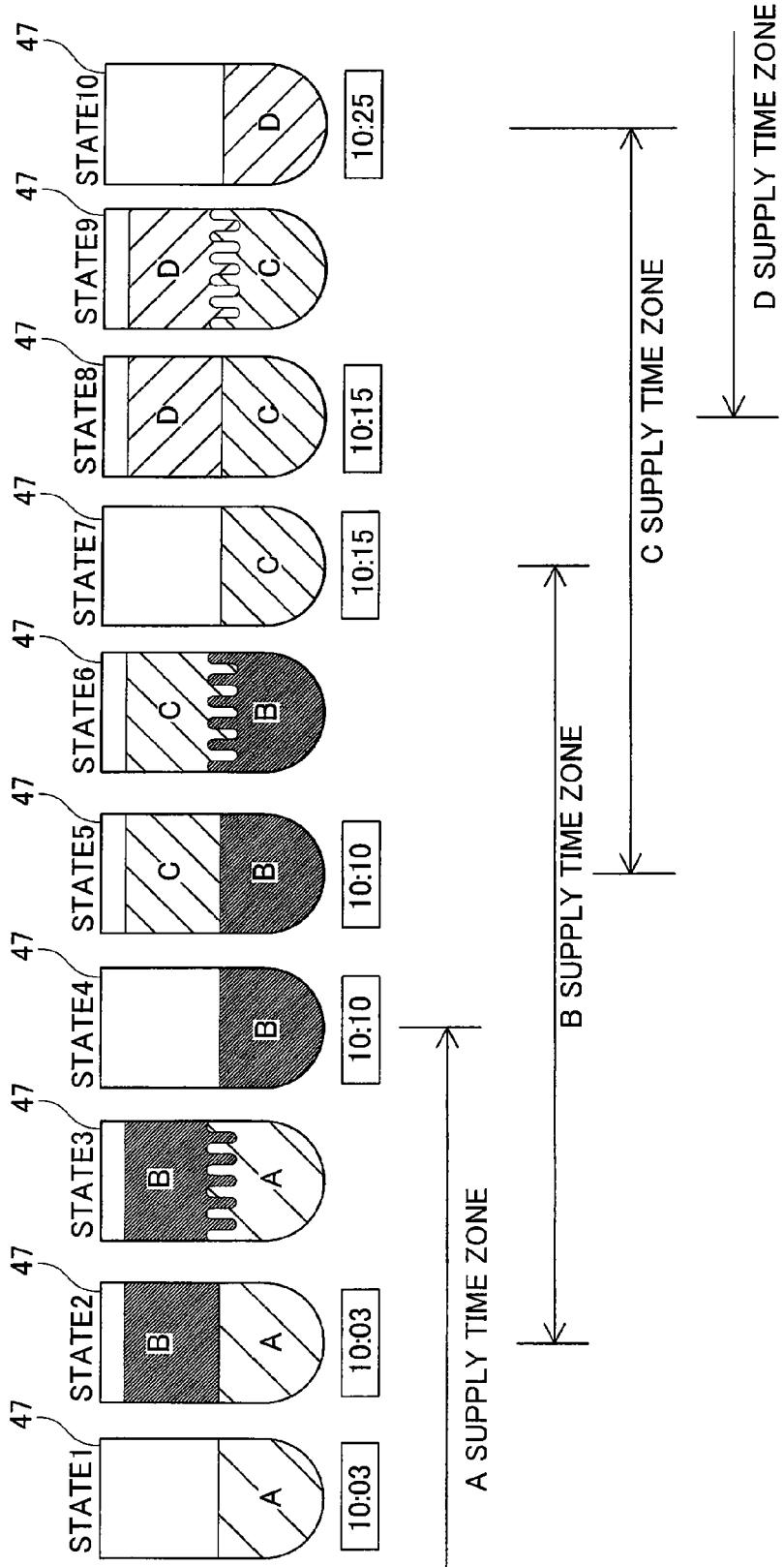
FIG. 15 is a conceptual diagram for illustrating a prepared reagent supply time zone in the reagent preparation apparatus according to the first embodiment of the present invention.

More specifically, a new reagent B of about 300 mL is supplied to the supply chamber 47 (state 2) when the residue of a reagent A in the supply chamber 47 reaches about 300 mL (state 1), as shown in FIG. 15. The date and the time of this moment correspond to the reagent preparation date. In other words, three past ten, Jan. 5, 2009 becomes the reagent preparation date of the reagent B in the case of FIG. 15. When the residue of the reagent A in the supply chamber 47 reaches about 300 mL (state 1), the new reagent B of about 300 mL is rapidly supplied to the supply chamber 47 (state 2), and hence the times of the state 1 and the state 2 substantially coincide with each other. In the first embodiment, therefore, it is assumed for the sake of convenience that there is no time difference between the time when the residue of the reagent A in the supply chamber 47 has reached about 300 mL and the time when the new reagent B of about 300 mL is supplied to the supply chamber 47.

After the reagent A and the reagent B are slightly mixed with each other in the supply chamber 47 (state 3), a reagent of about 300 mL is transported from the supply chamber 47 to the measurement portion 2. At this time, the reagent A and the reagent B are slightly mixed with each other in the supply chamber 47, and hence not only the reagent A, but also a small volume of the reagent B is contained in the reagent of about 300 mL transported to the measurement portion 2. However, the volume of the reagent B transported to the measurement portion 2 at this time is conceivably small, and hence it is assumed for the sake of convenience that only the reagent B of about 300 mL remains in the supply chamber 47 in the first embodiment.

The residue of the reagent B in the supply chamber 47 reaches about 300 mL in the state 4, and hence a new reagent C of about 300 mL is supplied to the supply chamber 47 (state 5). The current date (ten past ten, Jan. 5, 2009) becomes the reagent preparation date of the reagent C. The reagent B and the reagent C are slightly mixed with each other in the supply chamber 47 (state 6), and a reagent of about 300 mL is thereafter further transported from the supply chamber 47 to the measurement portion 2. At this time, it is assumed for the sake of convenience that only the reagent C of about 300 mL remains in the supply chamber 47, on the basis of the aforementioned idea. In other words, it is assumed that the reagent B has been entirely transported to the measurement portion 2 in the state 7. After the state 7, a new reagent D of about 300 mL is supplied to the supply chamber 47 (state 8). The current date (a quarter past ten, Jan. 5, 2009) becomes the reagent preparation date of the reagent D.

In this case, it is conceivable that the reagent B has been present in the supply chamber 47 between the state 2 (three past ten, Jan. 5, 2009) and the state 7 (a quarter past ten, Jan. 5, 2009), and hence the time zone (prepared reagent supply time zone) having a possibility that the reagent B has been transported from the supply chamber 47 to the measurement portion 2 becomes three past ten, Jan. 5, 2009 to a quarter past ten, Jan. 5, 2009. That is, the starting time of the prepared reagent supply time zone is the reagent preparation date of the target reagent B, and the ending time of the prepared reagent supply time zone is the reagent preparation date of the reagent D supplied to the supply chamber 47 after two reagents as viewed from the target reagent B. In other words, the reagent preparation date of the reagent D is so acquired that it becomes possible to acquire the prepared reagent supply time zone of the reagent B (whose reagent preparation result has been G (Good)) supplied to the supply chamber 47 at the time before the precedent one. Thus, the prepared reagent supply time zone of the reagent B is acquired on the basis of both of the reagent preparation date (three past ten, Jan. 5, 2009) of the reagent B and the reagent preparation date (a quarter past ten, Jan. 5, 2009) of the reagent D.

Observing the prepared reagent supply time zone of the reagent B from the viewpoint of the liquid volume of the reagent discharged from the supply chamber 47 (transported to the measurement portion 2), the prepared reagent supply time zone of the reagent B is the time zone from the time when the reagent B has begun to be supplied to the supply chamber 47 (state 2 (three past ten, Jan. 5, 2009)) up to the time when the same reagent of about 600 mL (reagent A of about 300 mL+reagent B of about 300 mL) as the storage volume of the supply chamber 47 is discharged from the supply chamber 47 (state 7 (a quarter past ten, Jan. 5, 2009).

Figure 13:
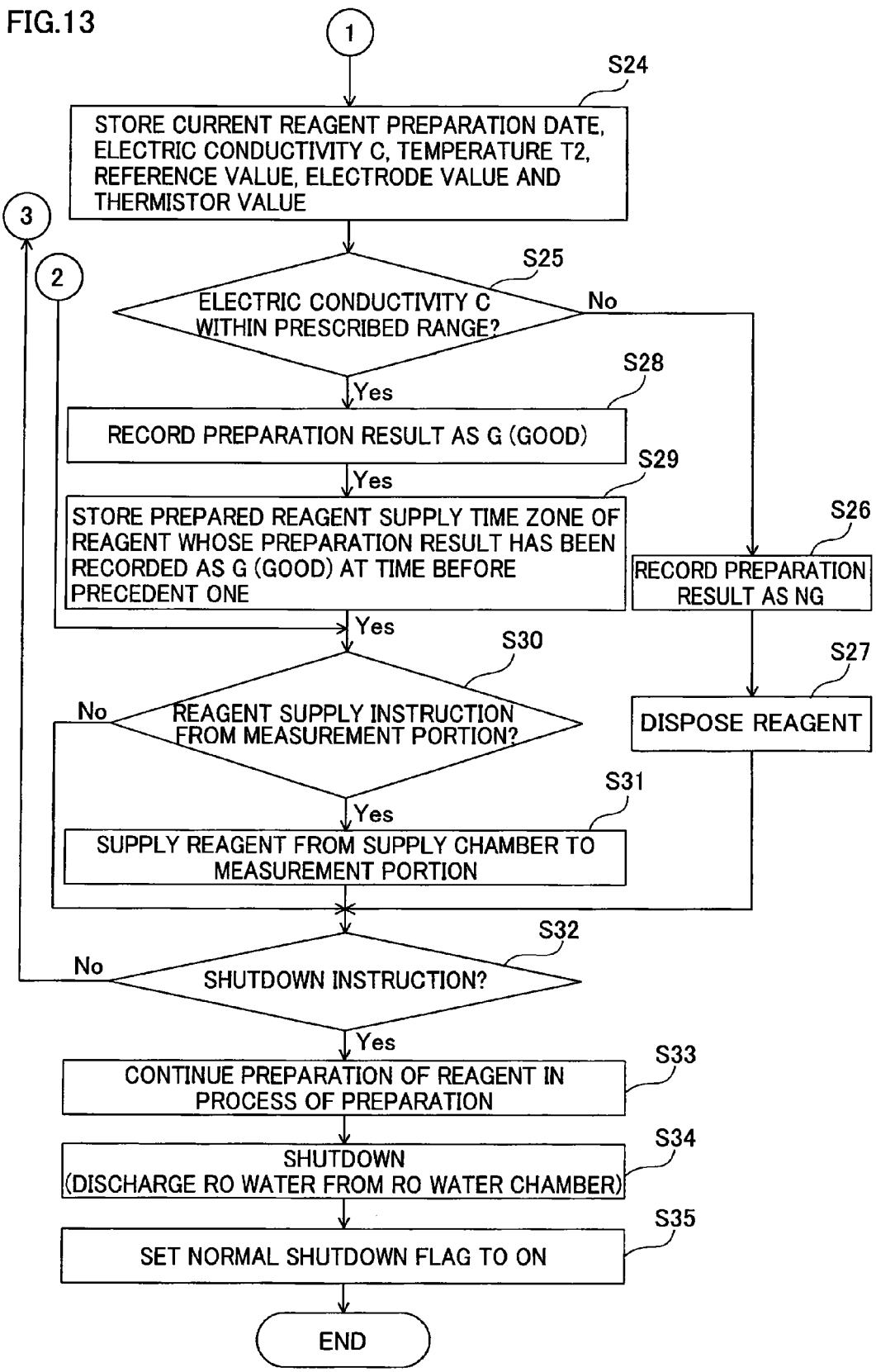
FIG. 13 is a flow chart for illustrating the reagent preparation processing operation of the reagent preparation apparatus according to the first embodiment of the present invention.

After the prepared reagent supply time zone is stored in the storage portion 49f at the step S29 in FIG. 13, whether or not there is a reagent supply instruction from the measurement portion 2 transmitted through the data processing portion 3 is determined by the CPU 49a at the step S30, and the process advances to a step S32 if there is no instruction. If there is the reagent supply instruction, the reagent in the supply chamber 47 is transported to the measurement portion 2 through the filter 471 by negative pressure force supplied from the measurement portion 2 at a step S31. Then, the presence or absence of a shutdown instruction from the user is determined by the CPU 49a at a step S32, and the process is shifted to the step S12 if there is no instruction.

If there is the shutdown instruction, the aforementioned operations are continued at a step S33 until the reagent in the process of preparation is finally transported to the supply chamber 47. More specifically, reagent preparation is continued through the operations of the aforementioned steps S20 to S29 if there is no reagent of the predetermined volume (at least about 300 mL and not more than about 600 mL) in the supply chamber 47, and hence it follows that a reagent diluted to a concentration different from the desired concentration remains in the channels, the dilution chamber 43 (44) and the stirring chamber 46 if the operations are stopped in the process of preparation. Therefore, it is possible to prevent the reagent diluted to the concentration different from the desired concentration from remaining in the channels, the dilution chamber 43 (44) and the stirring chamber 46 by making the preparation operations continued at the step S33.

Then, a shutdown is executed at a step S34. At this time, the RO water is discharged from the RO water chamber 42. Thus, it is possible to prevent the RO water from remaining in the RO water chamber 42 until the reagent preparation apparatus 4 is started next time. Thereafter the flag indicating that the shutdown has been normally performed is set to ON at a step S35, to terminate the reagent preparation processing operation.

A method of confirming a reagent preparation history is now described with reference to FIGS. 16 to 19.

Figure 16:
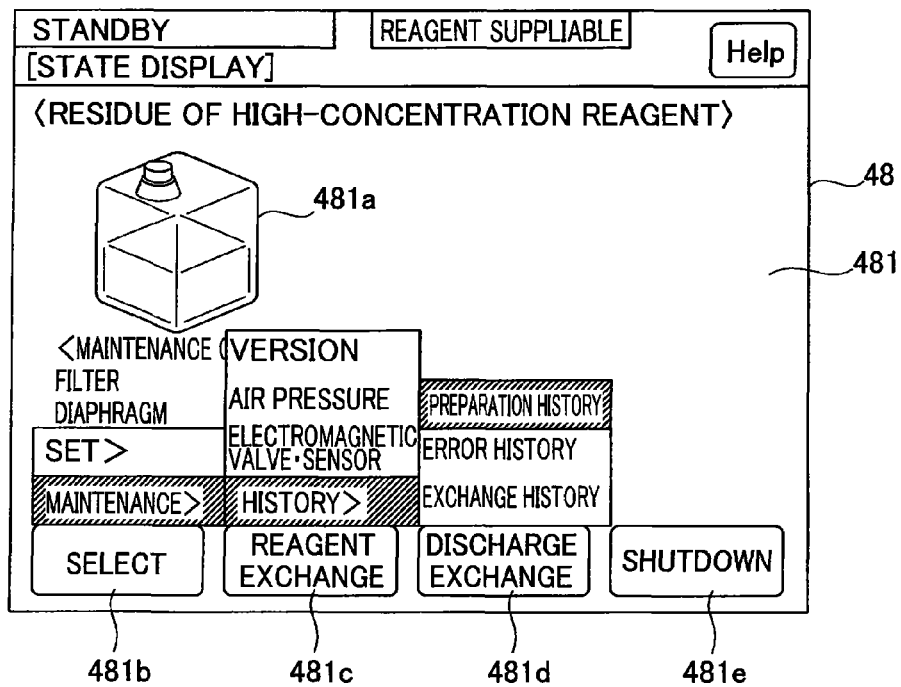
FIG. 16 is a diagram for illustrating a method of confirming a reagent preparation history in the reagent preparation apparatus according to the first embodiment of the present invention.
Figure 17:
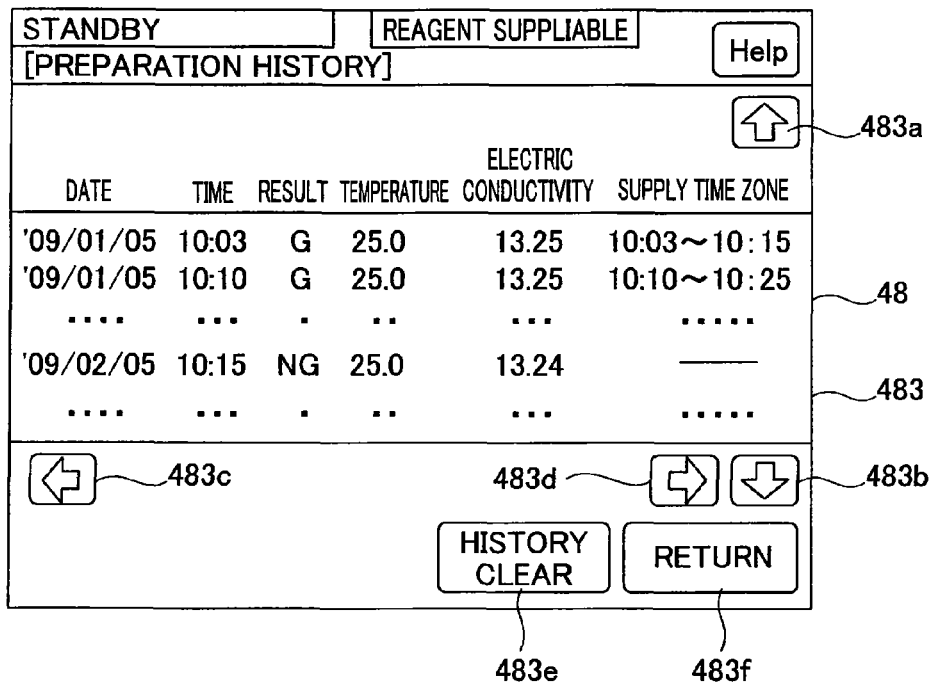
FIG. 17 is a diagram for illustrating the method of confirming the reagent preparation history in the reagent preparation apparatus according to the first embodiment of the present invention.

First, the user presses the select button 481b from the menu screen 481 displayed on the display portion 48 and successively selects maintenance, history and preparation history from a select menu, as shown in FIG. 16. When the user selects the preparation history, a preparation history first screen 483 is displayed on the display portion 48, as shown in FIG. 17. Reagent preparation dates (dates and times), reagent preparation results, temperatures at the times when reagent preparations have been completed, electric conductivity values at the times when the reagent preparations have been completed and prepared reagent supply time zones are displayed on the preparation history first screen 483. These are displayed on the basis of the contents of the reagent preparation list 492 of the storage portion 49f. A reagent whose reagent preparation result is NG is disposed without being transported to the supply chamber 47, and hence the same is not transported to the measurement portion 2. Therefore, a column of the prepared reagent supply time zone as to the reagent whose reagent preparation result is NG is blanked.

Upward and downward direction buttons 483a and 483b, left and right direction buttons 483c and 483d, a history clear button 483e and a return button 483f are also displayed on the preparation history first screen 483. The user can successively display preparation history data of respective prepared reagents displayed by five at a time in ascending order of the reagent preparation dates by pressing the upward and downward buttons 483a and 483b. Further, the user can delete the preparation history information of each prepared reagent by pressing the history clear button 483a. When the user presses the return button 483f, the precedent display screen is displayed. The user can read other items of the preparation history information of each prepared reagent by pressing the left and right direction buttons 483c and 483d.

When the user presses the right direction button 483d, a preparation history second screen 484 is displayed on the display portion 48, as shown in FIG. 18. Reagent preparation dates (dates and times), reference values, electrode values and thermistor values are displayed on the preparation history second screen 484. These are displayed on the basis of the contents of the reagent preparation list 492 of the storage portion 49f.

When the user further presses the right direction button 483d in the state making the preparation history second screen 484 displayed, a preparation history third screen 485 is displayed on the display portion 48, as shown in FIG. 19. Reagent preparation dates (dates and times), lot numbers of high-concentration reagents employed for reagent preparations, post-preparation expiration dates of the high-concentration reagents, use start days of the high-concentration reagents and post-opening expiration dates of the high-concentration reagents are displayed on the preparation history third screen 485. These are displayed on the basis of the contents of the reagent management list 491 of the storage portion 49f. When the user further presses the right direction button 483d in the state making the preparation history third screen 485 displayed, the display screen returns to the preparation history first screen 483 shown in FIG. 17. When the user presses the left direction button 483c, the preparation history first screen 483, the preparation history second screen 484 and the preparation history third screen 485 are displayed in the order reverse to that in the case of pressing the right direction button 483d. Thus, the user can confirm the high-concentration reagent information and the reagent preparation history information by browsing the preparation history first screen 483, the preparation history second screen 484 and the preparation history third screen 485.

When the user successively selects the maintenance, the history and error history of the select menu on the menu screen 481 shown in FIG. 16, an unshown error history screen is displayed, so that it is possible to confirm various error histories in the reagent preparation apparatus 4. When the user successively selects the maintenance, the history and exchange history of the select menu on the menu screen 481 shown in FIG. 16, an unshown exchange history screen is displayed, so that it is possible to confirm an exchange history of the high-concentration reagent tank 5 based on the reagent management list 491 of the storage portion 49f.

According to the first embodiment, as hereinabove described, the CPU 49a acquiring the reagent information related to the prepared reagent and acquiring the prepared reagent supply time zone of the prepared reagent to the measurement portion 2 and the display portion 48 displaying the reagent information and the prepared reagent supply time zone are so provided that when what sort of reagent has been supplied to the measurement portion 2 can be easily confirmed. Thus, it becomes easy to acquire information of a reagent employed for measurement in a case where the reliability of a measurement result is low, whereby pursuance of the cause of the reduction in the reliability of the measurement result becomes easy.

According to the first embodiment, the CPU 49a is formed to acquire the electric conductivity of the prepared reagent so that the quality of the reagent can be confirmed after specifying the reagent employed for the measurement in the measurement portion 2, whereby the pursuance of the cause of the reduction in the reliability of the measurement result can be more easily performed.

According to the first embodiment, the CPU 49a is formed to acquire the prepared reagent supply time zone on the basis of the reagent preparation date so that the prepared reagent supply time zone can be acquired on the basis of the reagent preparation date, whereby the prepared reagent supply time zone may not be measured and acquired separately from the reagent preparation date.

According to the first embodiment, the CPU 49*a* is formed to acquire the time zone having the possibility that the prepared reagent has been supplied to the measurement portion 2 as the prepared reagent supply time zone so that a reagent having a possibility of being actually employed for the measurement in the measurement portion 2 can be easily specified, whereby the pursuance of the cause of the reduction in the reliability of the measurement result becomes easy.

According to the first embodiment, the CPU 49*a* is formed to acquire the high-concentration reagent information related to the high-concentration reagent as the reagent information while the display portion 48 is formed to output the high-concentration reagent information so that with which high-concentration reagent the reagent employed for the measurement has been prepared can be easily confirmed on the basis of the high-concentration reagent information of the high-concentration reagent contained in the prepared reagent, whereby the pursuance of the cause of the reduction in the reliability of the measurement result becomes easier. Further, with which lot of high-concentration reagent the reagent has been prepared can be easily specified by confirming the lot number of the high-concentration reagent.

According to the first embodiment, the bar code reader 50 reading the bar codes 50*b* of the label 50*a* stuck to the high-concentration reagent tank 5 is provided and the high-concentration reagent information is acquired by the CPU 49*a* on the basis of the information read by the bar code reader 50, whereby the high-concentration reagent information can be easily acquired by employing the bar code reader 50.

Second Embodiment

A second embodiment is now described with reference to FIGS. 20 and 21. In this second embodiment, reagent preparation apparatus 500 including an RO water preparation portion 7 therein is described, dissimilarly to the aforementioned first embodiment.

Figure 20:
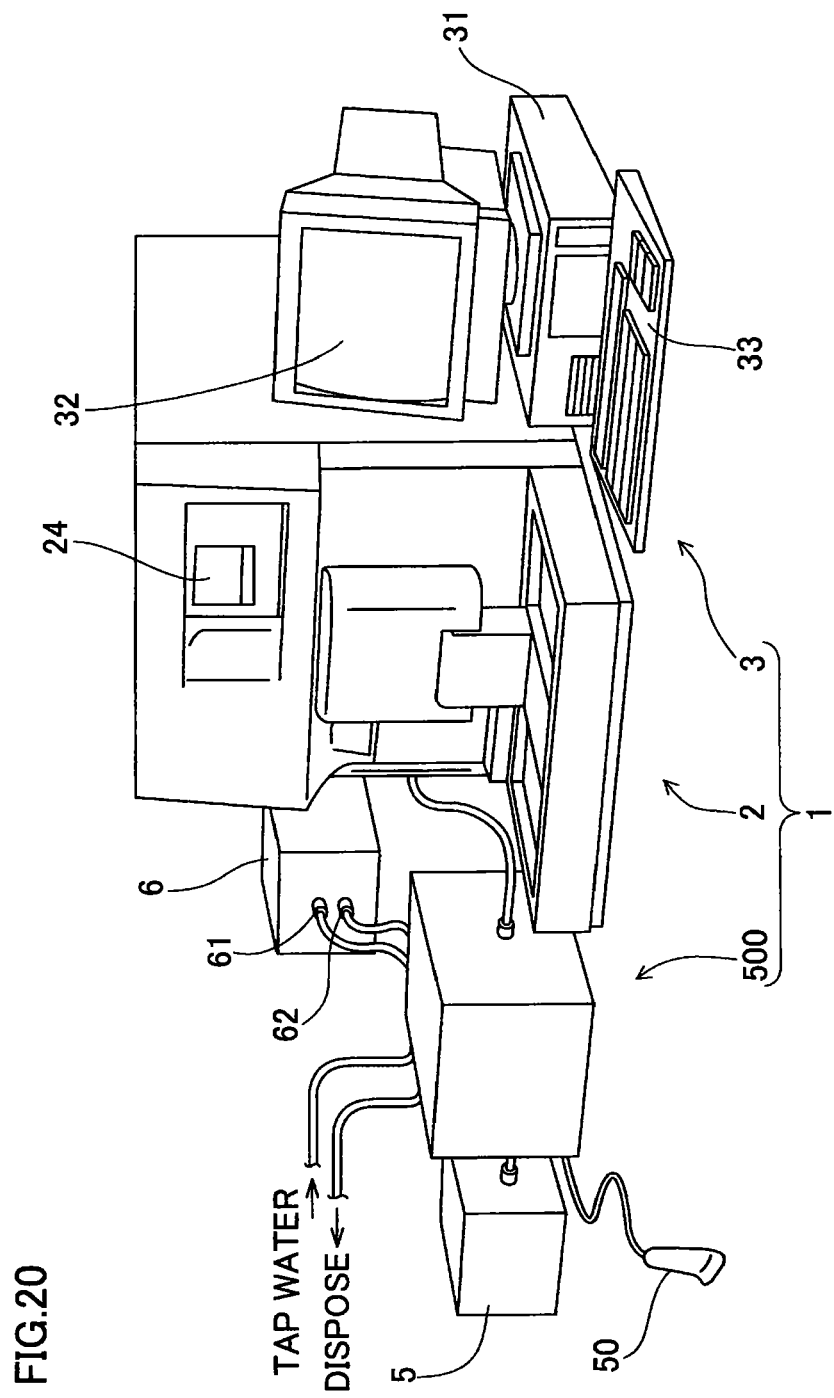
FIG. 20 is a perspective view showing a used state of reagent preparation apparatus according to a second embodiment of the present invention.

A blood specimen processing system 1 is constituted of a measurement portion 2 having a function of performing measurement of blood, a data processing portion 3 obtaining an analytical result by analyzing measurement data output from the measurement portion 2 and the reagent preparation apparatus 500 preparing a reagent employed for processing the specimen, as shown in FIG. 20.

Figure 21:
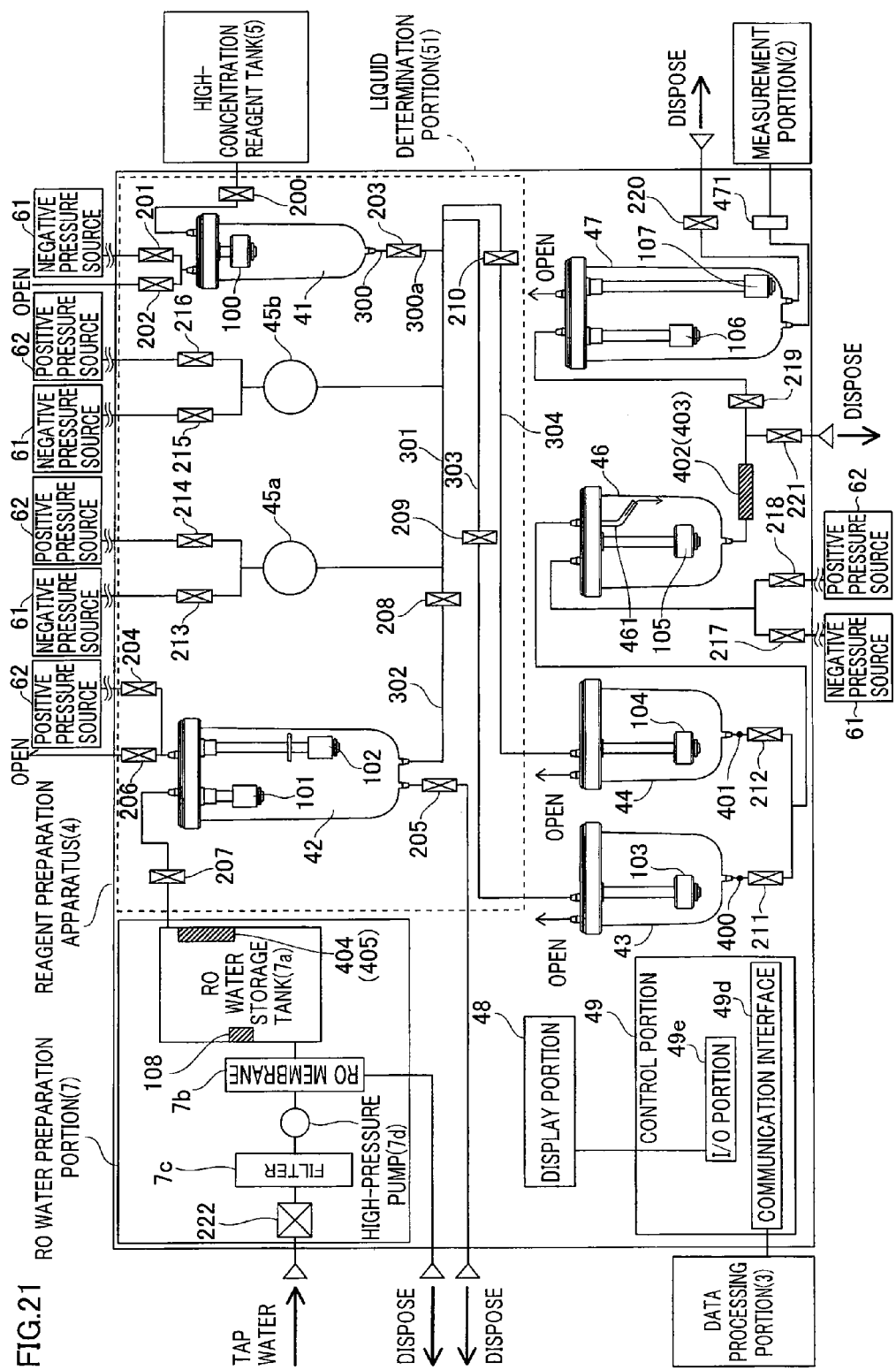
FIG. 21 is a schematic diagram showing the structure of the reagent preparation apparatus according to the second embodiment shown in FIG. 20.

According to the second embodiment, the reagent preparation apparatus 500 is formed to prepare the reagent employed for hemanalysis by diluting a high-concentration reagent to a desired concentration with RO water prepared by the RO water preparation portion 7 provided therein, as shown in FIGS. 20 and 21.

No display portion is provided on the reagent preparation apparatus 500, dissimilarly to the aforementioned first embodiment. Therefore, the user starts and shuts down the reagent preparation apparatus 500 with an input device 33 of the data processing portion 3.

The reagent preparation apparatus 500 is formed to transmit various types of information (high-concentration reagent information and reagent preparation history information) recorded in a reagent management list 491 and a reagent preparation list 492 of a storage portion 49*f* through a communication interface 49*d*. Thus, the user can confirm the high-concentration reagent information and the reagent preparation history information on a display portion 32 of the data processing portion 3.

The remaining structure of the second embodiment is similar to that of the aforementioned first embodiment.

According to the second embodiment, as hereinabove described, the RO water preparation portion 7 is provided in the reagent preparation apparatus 500, whereby the structure of the overall blood specimen processing system 1 can be simplified.

The remaining effects of the second embodiment are similar to those of the aforementioned first embodiment.

The embodiments disclosed this time must be considered as illustrative in all points and not restrictive. The range of the present invention is shown not by the above description of the embodiments but by the scope of claims for patent, and all modifications within the meaning and range equivalent to the scope of claims for patent are included.

For example, while the example of displaying the high-concentration reagent information and the reagent preparation history information on the display portion as the reagent information has been shown in each of the aforementioned first and second embodiments, the present invention is not restricted to this, but RO water information consisting of the electric conductivity or the like of the RO water prepared in the RO water preparation portion 7 may be displayed on the display portion as the reagent information, in addition to the high-concentration reagent information and the reagent preparation history information. Alternatively, the RO water information and the reagent preparation history information may be displayed on the display portion without displaying the high-concentration reagent information.

While the example in which the reagent preparation history information has the structure including the reagent preparation date, the electric conductivity, the temperature, the reference value, the electrode value, the thermistor value, the reagent preparation result and the prepared reagent supply time zone has been shown in each of the aforementioned first and second embodiments, the present invention is not restricted to this, but the reagent preparation history information may have a structure not including the aforementioned information other than the prepared reagent supply time zone, or may have a structure further including other information other than the above, so far as the reagent preparation history information includes the prepared reagent supply time zone.

While the example of the structure of acquiring the prepared reagent supply time zone on the basis of the reagent preparation date has been shown in each of the aforementioned first and second embodiments, the present invention is not restricted to this, but a sensor may be provided in the path reaching the measurement portion from the supply chamber for acquiring a time when the reagent transported from the supply chamber to the measurement portion has passed through the sensor as a prepared reagent supply time.

While the reagent consisting of the high-concentration reagent and the RO water (pure water) has been shown as an example of the predetermined reagent in each of the aforementioned first and second embodiments, the present invention is not restricted to this, but the reagent may consist of other types of liquids different from the high-concentration reagent and the RO water (pure water).

While the example of regarding the time zone from the time when the reagent has begun to be supplied to the supply chamber up to the time when the reagent of the same volume as the storage volume of the supply chamber is discharged from the supply chamber as the prepared reagent supply time zone has been shown in each of the aforementioned first and second embodiments, the present invention is not restricted to this, but a time zone from the time when the reagent has begun to be supplied to the supply chamber up to a time when a reagent of a volume, such as a volume of 1.5 times the storage volume of the supply chamber, for example, different from the storage volume of the supply chamber is discharged from the supply chamber or a time zone up to a time when a reagent of a volume different from the volume of 1.5 times the storage volume of the supply chamber is discharged from the supply chamber may be regarded as the prepared reagent supply time zone. In this case, the prepared reagent supply time zone of the corresponding reagent can be more precisely acquired when selecting a time zone up to a time when a reagent of a volume larger than the storage volume of the supply chamber is discharged from the supply chamber.

While the example of the structure separately providing the measurement portion and the data processing portion has been shown in each of the aforementioned first and second embodiments, the present invention is not restricted to this, but the measurement portion and the data processing portion may constitute one blood specimen analyzer.

While the example of displaying the reagent information (high-concentration reagent information and reagent preparation history information) on the display portion of the reagent preparation apparatus has been shown in the aforementioned first embodiment, the present invention is not restricted to this, but the reagent preparation apparatus may transmit the reagent information (high-concentration reagent information and reagent preparation history information) to the data processing portion to display the reagent information (high-concentration reagent information and reagent preparation history information) on the display portion of the data processing portion, similarly to the structure of the aforementioned second embodiment.

While the example of displaying the reagent information (high-concentration reagent information and reagent preparation history information) on the display portion of the data processing portion has been shown in the aforementioned second embodiment, the present invention is not restricted to this, but a display portion may be provided on the reagent preparation apparatus to display the reagent information (high-concentration reagent information and reagent preparation history information) on the display portion of the reagent preparation apparatus, similarly to the structure of the aforementioned first embodiment.

While the example of the structure regarding the date when the prepared reagent has passed through the conductivity sensor as the reagent preparation date has been shown in each of the aforementioned first and second embodiments, the present invention is not restricted to this, but may have a structure of acquiring the reagent preparation date on the basis of a sensing result of the float switch of the supply chamber, or may have a structure of acquiring the reagent preparation date by separately providing a sensor for acquiring the reagent preparation date on the supply chamber.

Figure 22:
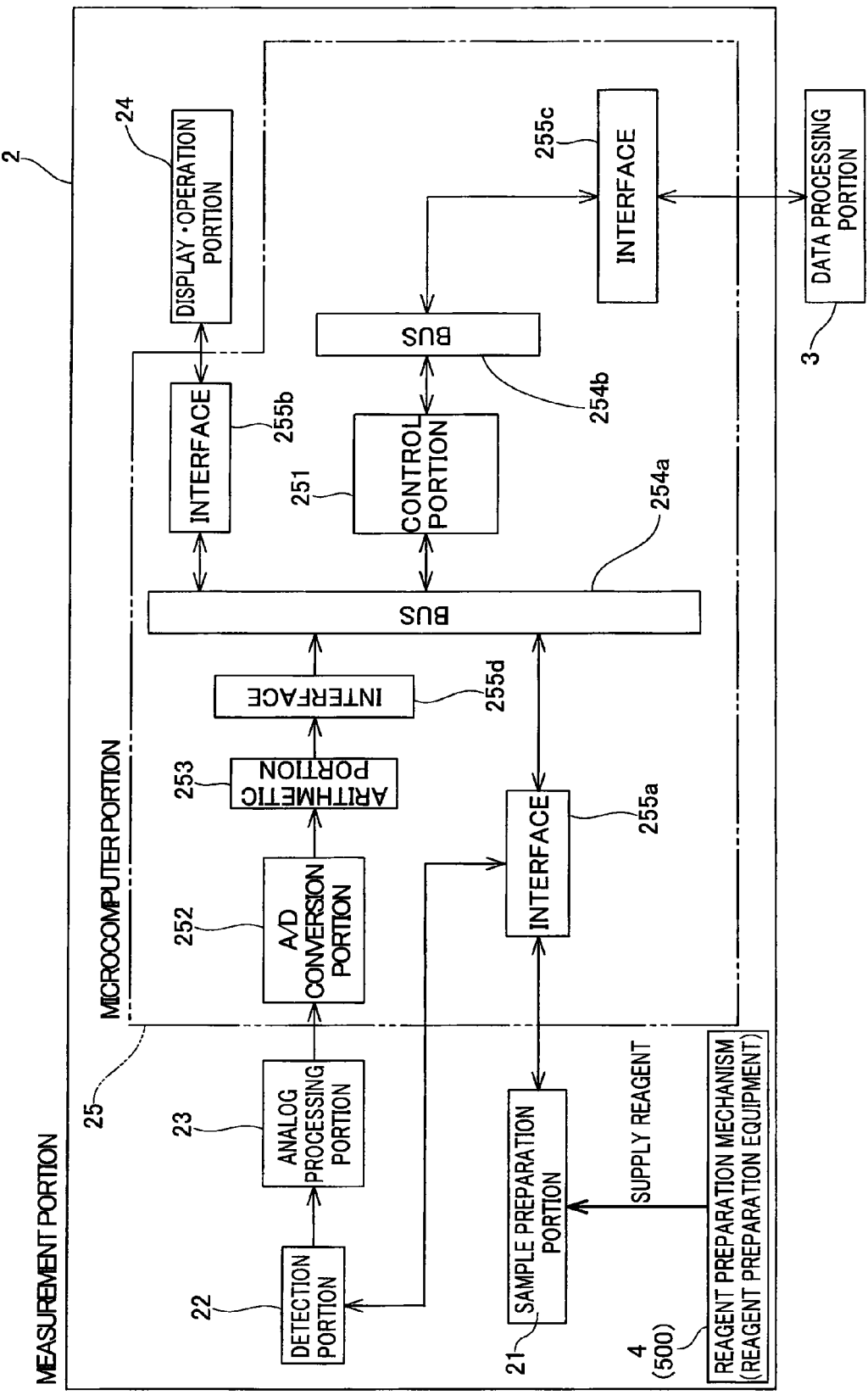
FIG. 22 is a block diagram showing a modification of the reagent preparation apparatus according to each of the first embodiment shown in FIG. 1 and the second embodiment shown in FIG. 20.

While the reagent preparation apparatus set separately from the measurement portion has been shown as an example of the reagent preparation apparatus in each of the aforementioned first and second embodiments, the present invention is not restricted to this, but may be reagent preparation apparatus provided in a measurement portion for functioning as a reagent preparation mechanism, as shown in FIG. 22. While there is a blood cell counter, an immunoassay apparatus or a smear preparation apparatus, for example, as a measurement portion (apparatus) including a reagent preparation mechanism in this manner, it is suitable to the blood cell counter using a large volume of dilution liquid, in particular.

While the reagent preparation apparatus in which reagents prepared from high-concentration reagents whose lot numbers are different from each other are mixed with each other in the supply chamber has been shown in each of the aforementioned first and second embodiments, the present invention is not restricted to this, but may be reagent preparation apparatus disposing a mixed liquid of a high-concentration reagent or a mixed liquid of the high-concentration reagent and pure water stored in each chamber when exchanging the high-concentration reagent. Thus, no reagents having different lot numbers are mixed with each other in the chamber, whereby more correct supply time information can be acquired.

While the specimen processing system in which the supply time information is displayed on the display of the reagent preparation apparatus and the analytical result of the specimen is displayed on the display of the data processor has been shown in the aforementioned first embodiment, the present invention is not restricted to this, but may be a specimen processing system transmitting acquired supply time information to a data processor every time reagent preparation apparatus acquires the supply time information and outputting an analytical result of a specimen, a measurement time of the specimen and the supply time information received from the reagent preparation apparatus in association with each other by the data processor. Thus, unified management of information by the data processor becomes possible.

While the bar code reader 50 has been shown as an example of the information read portion in each of the aforementioned first and second embodiments, the present invention is not restricted to this, but may have an information read portion such as a QR code reader capable of reading a QR code (registered trademark) including related to a high-concentration reagent, for example, other than the bar code reader.

While the example of preparing the reagent from the high-concentration reagent and the RO water has been shown in each of the first and second embodiments, a substance mixed with the RO water is not limited to a liquid. The substance mixed with the RO water may be freeze-dried reagent powder or a reagent tablet which can be dissolved in the RO water.

What is claimed is:

1. A reagent preparation apparatus for preparing a predetermined reagent to be supplied to a measurement portion configured to measure a specimen with the predetermined reagent, the reagent preparation apparatus comprising:
  a stirring chamber configured to prepare the predetermined reagent using a first liquid and a second liquid;
  a supply chamber in fluid communication with the stirring chamber and the measurement portion, the stirring chamber being configured to supply the predetermined reagent to the supply chamber, the supply chamber being configured to store the predetermined reagent supplied by the stirring chamber and to supply the predetermined reagent to the measurement portion;
  a sensor provided in a flow path between the stirring chamber and the supply chamber, the sensor being in fluid communication with the stirring chamber and the supply chamber, the sensor being configured to measure a property of the predetermined reagent prepared by the stirring chamber to obtain reagent information of the predetermined reagent; and
  a control portion comprising a processor programmed to:
    receive the reagent information from the sensor in electrical communication with the processor,
    determine supply time information comprising a time zone having a possibility that the predetermined reagent was supplied to the measurement portion on the basis of a plurality of reagent preparation dates including when the predetermined reagent passed through the sensor provided in the flow path between the stirring chamber and the supply chamber, and output the reagent information and the supply time information.

2. The reagent preparation apparatus according to claim 1, wherein the sensor is a conductivity sensor configured to measure electric conductivity of the predetermined reagent, and the processor is further programmed to receive the electric conductivity measured by the sensor as the reagent information.

3. The reagent preparation apparatus according to claim 1, wherein the sensor is a conductivity sensor configured to measure electric conductivity of the predetermined reagent supplied by the stirring chamber to the supply chamber.

4. The reagent preparation apparatus according to claim 3, wherein the processor is further programmed to determine a target electric conductivity value for the predetermined reagent and to control supply of the predetermined reagent from the stirring chamber to the supply chamber such that the predetermined reagent is supplied to the supply chamber when the electric conductivity measured by the conductivity sensor is within a predetermined range of the target electric conductivity value and the predetermined reagent is discarded by the stirring chamber when the electric conductivity measured by the conductivity sensor is not within the predetermined range of the target electric conductivity value.

5. The reagent preparation apparatus according to claim 1, wherein the processor is further programmed to store, in the memory, preparation time information comprising times when separate amounts of the predetermined reagent passed through the sensor provided in the flow path between the stirring chamber and the supply chamber, and determine the supply time information on the basis of the preparation time information stored in the memory.

6. The reagent preparation apparatus according to claim 1, the supply chamber having a predetermined storage volume, wherein the time zone is defined from a time when the predetermined reagent began to be supplied to the supply chamber after a predetermined amount of the reagent remained in the supply chamber up to a time when an amount of the reagent in a volume substantially identical to the predetermined storage volume of the supply chamber was discharged from the supply chamber to the measurement portion.

7. The reagent preparation apparatus according to claim 1, wherein the first liquid is an undiluted reagent, and the processor is further programmed to obtain undiluted reagent information related to the undiluted reagent, and output the undiluted reagent information.

8. The reagent preparation apparatus according to claim 7, further comprising an information read portion configured to read the undiluted reagent information from a reagent vessel storing the undiluted reagent, wherein the undiluted reagent information is obtained by the processor from the information read portion.

9. The reagent preparation apparatus according to claim 7, wherein the undiluted reagent information includes a lot number of the undiluted reagent.

10. The reagent preparation apparatus according to claim 7, wherein the undiluted reagent information includes expiration date information related to an expiration date of the undiluted reagent.

11. The reagent preparation apparatus according to claim 1, further comprising a memory, wherein the processor is programmed to store the received reagent information and the determined supply time information in the memory, and is programmed to output the reagent information and the supply time information stored in the memory responsive to an instruction by a user.

12. A reagent preparation apparatus for preparing a predetermined reagent, the reagent preparation apparatus comprising:

preparing means for preparing the predetermined reagent using a first liquid and a second liquid;

supply means for supplying the predetermined reagent prepared by the preparing means to a measurement means for measuring a specimen with the predetermined reagent, the supplying means being in communication with the preparing means and the measurement means;

acquiring means for acquiring reagent information related to the predetermined reagent, the acquiring means being in communication with the preparing means and the supply means;

means for determining supply time information comprising a time zone having a possibility that the predetermined reagent was supplied to the measurement means on the basis of a plurality of reagent preparation dates including when the predetermined reagent passed through the acquiring means between the preparing means and the supply means; and means for outputting the reagent information and the supply time information.

13. A specimen processing system comprising:

a measurement portion configured to measure a specimen with a predetermined reagent;

a stirring chamber configured to prepare the predetermined reagent using a first liquid and a second liquid different from the first liquid;

a supply chamber in fluid communication with the stirring chamber and the measurement portion, the stirring chamber being configured to supply the predetermined reagent to the supply chamber, the supply chamber being configured to store the predetermined reagent supplied by the stirring chamber and to supply the predetermined reagent to the measurement portion;

a sensor provided in a flow path between the stirring chamber and the supply chamber, the sensor being in fluid communication with the stirring chamber and the supply chamber, the sensor being configured to measure a property of the predetermined reagent prepared by the stirring chamber to obtain reagent information of the predetermined reagent; and a control portion comprising a processor programmed to:

receive the reagent information from the sensor in electrical communication with the processor, determine supply time information comprising a time zone having a possibility that the predetermined reagent was supplied to the measurement portion on the basis of a plurality of reagent preparation dates including when the predetermined reagent passed through the sensor provided in the flow path between the stirring chamber and the supply chamber, and output the reagent information and the supply time information.

14. A reagent preparation apparatus for preparing a predetermined reagent to be supplied to a measurement portion configured to measure a specimen with the predetermined reagent, the reagent preparation apparatus comprising:

a stirring chamber configured to prepare the predetermined reagent using a first liquid and a second liquid;

a supply chamber in fluid communication with the stirring chamber and the measurement portion, the stirring chamber being configured to supply the predetermined reagent to the supply chamber, the supply chamber being configured to store the predetermined reagent supplied by the stirring chamber and to supply the predetermined reagent to the measurement portion;

a sensor provided in a flow path between the stirring chamber and the supply chamber, the sensor being in fluid communication with the stirring chamber and the supply chamber, the sensor being configured to measure a property of the predetermined reagent prepared by the stirring chamber to obtain reagent information of the predetermined reagent;

a memory; and a processor programmed to:

store, in the memory, the reagent information received from the sensor in electrical communication with the processor, store, in the memory, supply time information comprising a time zone having a possibility that the predetermined reagent was supplied to the measurement portion, the supply time information having been determined by the processor on the basis of a plurality of reagent preparation dates including when the predetermined reagent passed through the sensor provided in the flow path between the stirring chamber and the supply chamber, and responsive to an instruction by a user output, the reagent information and the supply time information stored in the memory.

* * * * *